US012746145B2

(12) United States Patent
Liu et al.

(10) Patent No.: US 12,746,145 B2
(45) Date of Patent: Sep. 29, 2026

(54) HUMAN INTERFACE DEVICE FOR URINARY RELIEF SYSTEM

(71) Applicant: B/E Aerospace, Inc., Winston Salem, NC (US)

(72) Inventors: Lily Liu, Sammamish, WA (US); Hsin-I Tsai, Newport Pagnell (GB); Travis John Vaninetti, Bothell, WA (US)

(73) Assignee: B/E Aerospace, Inc., Winston Salem, NC (US)

( * ) Notice: Subject to any disclaimer, the term of this patent is extended or adjusted under 35 U.S.C. 154(b) by 788 days.

(21) Appl. No.: 18/123,174

(22) Filed: Mar. 17, 2023

(65) Prior Publication Data

US 2024/0307214 A1 Sep. 19, 2024

(51) Int. Cl.
*A61F 5/455* (2006.01)
*A61F 5/44* (2006.01)

(52) U.S. Cl.
CPC .......... *A61F 5/4556* (2013.01); *A61F 5/4401* (2013.01)

(58) Field of Classification Search
CPC .......... A61F 5/4556; A61F 5/4401
USPC .......... 604/327
See application file for complete search history.

(56) References Cited

U.S. PATENT DOCUMENTS 4,257,418 A * 3/1981 Hessner .......... A61F 13/51121 604/397
4,484,917 A 11/1984 Blackmon
4,610,675 A 9/1986 Triunfol
4,753,644 A * 6/1988 Cottenden .......... A61F 5/4401 604/378
4,799,928 A * 1/1989 Crowley .......... A61F 5/455 604/319
4,886,508 A * 12/1989 Washington .......... A61F 5/455 604/347
4,937,890 A * 7/1990 Tafur .......... A47K 11/12 604/350
5,002,541 A 3/1991 Conkling et al.
5,632,736 A * 5/1997 Block .......... A61F 5/455 206/581
6,551,292 B1 4/2003 D'Acchioli et al.
7,335,189 B2 2/2008 Harvie
10,806,623 B2 10/2020 VanMiddendorp et al.
(Continued)

FOREIGN PATENT DOCUMENTS

CN 110559121 12/2019
DE 29514400 11/1995
(Continued)

OTHER PUBLICATIONS

European Patent Office, European Search Report dated Jul. 4, 2024 in Application No. 24152435.4.

*Primary Examiner* — Andrew J Mensh
(74) *Attorney, Agent, or Firm* — SNELL & WILMER L.L.P.

(57) ABSTRACT

A human interface for a urinary relief system is disclosed herein. The human interface includes a body including a top, a bottom, a front, a back, a first side, and a second side, a fluid cavity defined by the bottom, the front, the back, the first side, and the second side, the fluid cavity open through an opening in the top of the body, and an outlet extending from the fluid cavity and through the bottom, the outlet located near the back and centered between the first side and the second side.

19 Claims, 24 Drawing Sheets

(56) References Cited

U.S. PATENT DOCUMENTS

| | | | | |
|---|---|---|---|---|
| 11,583,434 | B1 | 2/2023 | Cimino | |
| 2002/0026161 | A1 | 2/2002 | Grundke et al. | |
| 2003/0195484 | A1 * | 10/2003 | Harvie | A61F 5/455<br>604/355 |
| 2007/0185465 | A1 | 8/2007 | Campbell et al. | |
| 2010/0262097 | A1 * | 10/2010 | Hildeberg | A61L 15/46<br>604/360 |
| 2017/0281399 | A1 * | 10/2017 | VanMiddendorp | A61M 1/80 |
| 2022/0387001 | A1 | 12/2022 | Askenazi et al. | |
| 2024/0269010 | A1 * | 8/2024 | Powers | A61F 13/15739 |

FOREIGN PATENT DOCUMENTS

| | | | |
|---|---|---|---|
| WO | 2005089687 | 9/2005 | |
| WO | 2021211568 | 10/2021 | |
| WO | WO-2021211568 A1 * | 10/2021 | A61F 5/4556 |

* cited by examiner

HUMAN INTERFACE DEVICE FOR URINARY RELIEF SYSTEM

GOVERNMENT LICENSE RIGHTS

This disclosure was made with government support under contract No. FA8606-22-9-0002 awarded by the United States Air Force. The government has certain rights in the disclosure.

FIELD

The present disclosure generally relates urinary relief systems, and more specifically, to a human interface for urinary relief systems.

BACKGROUND

Aircrew often need to urinate multiple times during flights without removing restraint systems and flight equipment. Current flight length profiles and air refueling abilities have led to longer flight times for aircrew. As a result, some aircrew, especially female aircrew, resort to ingesting fewer liquids to reduce the need to urinate, resulting in dehydration. A safe, reliable, and effective system to provide aircrew, especially female aircrew, the capability of bladder relief during flight is sought.

SUMMARY

Disclosed herein is a human interface for a urinary relief system. The human interface includes a body including a top, a bottom, a front, a back, a first side, and a second side, a fluid cavity defined by the bottom, the front, the back, the first side, and the second side, the fluid cavity open through an opening in the top of the body, and an outlet extending from the fluid cavity and through the bottom, the outlet located near the back and centered between the first side and the second side.

In various embodiments, the human interface further includes a funnel formed in the fluid cavity, the funnel located near the back, the outlet fluidly coupled to the fluid cavity through the funnel. In various embodiments, the human interface further includes a pad having a pad body, a first wing, and a second wing, the first wing extending from a first portion of the pad body and the second wing extending from a second portion of the pad body. In various embodiments, the pad body includes a first end, a mid-point, and second end, the first portion of the pad body extending from the first end to the mid-point, the second portion of the pad body extending from the mid-point to the second end, wherein the pad body is configured to fold about the mid-point. In various embodiments, the pad is configured to be inserted into the fluid cavity and below the top of the body, the mid-point of the pad body being adjacent the front of the body, the first end and the second end of the pad body being adjacent the back.

In various embodiments, the human interface further includes a first indent formed in the first side of the top of the body, the first indent configured to receive the first wing and a second indent formed in the second side of the top of the body, the second indent configured to receive the second wing. In various embodiments, the pad body includes a pad front, a pad back, a first pad side, and a second pad side, the pad front, the pad back, the first pad side, and the second pad side defining a pad opening through the pad.

In various embodiments, the pad is configured to be coupled to the top of the body, the pad opening aligning with the opening in the top. In various embodiments, the first side has a first curve extending toward the fluid cavity along the first side from the back to the front, and wherein the second side has a second curve extending toward the fluid cavity along the second side from the back to the front. In various embodiments, the top is curved upward from the back to the front, the front being higher than the back.

Also disclosed herein is a urinary relief system. The urinary relief system includes a control unit, a storage device coupled to the control unit, and a human interface device coupled to the storage device. The human interface device includes a tray including a top, a bottom, a front, a back, a first side, and a second side, a fluid cavity defined by the bottom, the front, the back, the first side, and the second side, the fluid cavity open through an opening in the top of the tray, and an outlet extending from the fluid cavity and through the bottom and adjacent the back of the tray, the outlet extending toward the front of the tray.

In various embodiments, the outlet is centered between the first side and the second side. In various embodiments, the outlet is located adjacent the first side of the tray. In various embodiments, the urinary relief system further includes a pad having a linear body with a first end, a mid-point, and a second end, a first wing extending from the first end to the mid-point and extending outward from the linear body, and a second wing extending from the mid-point to the second end and extending outward from the linear body, wherein the pad is configured to be inserted into the fluid cavity, the first wing is configured to extend over the top on the first side, and the second wing is configured to extend over the top on the second side.

In various embodiments, the urinary relief system further includes a pad having an oval body, a pad opening formed therethrough, the pad configured to be coupled to the top of the tray, a first wing extending from a first side of the pad, and a second wing extending from a second side of the pad. In various embodiments, the urinary relief system further includes a pad having a pad front, a pad back, a first pad side, and a second pad side, a pad opening extending through the pad, wherein the pad is disposed around an outer surface of the tray and below the top of the tray. In various embodiments, the urinary relief system further includes a ring formed around the outer surface of the tray and below the top of the tray and a channel defined by the top of the tray and the ring, wherein the pad is located in the channel.

Also disclosed herein is a human interface assembly including a body having a front, a back, a bottom, a top, a first side, and a second side, the top having an opening formed therethrough, a fluid cavity formed in the body and defined by the front, the back, the bottom, the top, the first side, and the second side, and an outlet formed near the back of the body, the outlet extending from the fluid cavity and through the bottom of the body.

In various embodiments, the human interface assembly further includes a pad coupled to the body, the pad is configured to be inserted into the fluid cavity and below the top of the body, the pad including a wing configured to extend over the top of the body. In various embodiments, the human interface assembly further includes a funnel located near the back of the body, the funnel coupling the fluid cavity to the outlet, wherein the outlet extends out toward the first side of the body, the outlet including an outlet opening toward the front of the body.

The foregoing features and elements may be combined in any combination, without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1A:
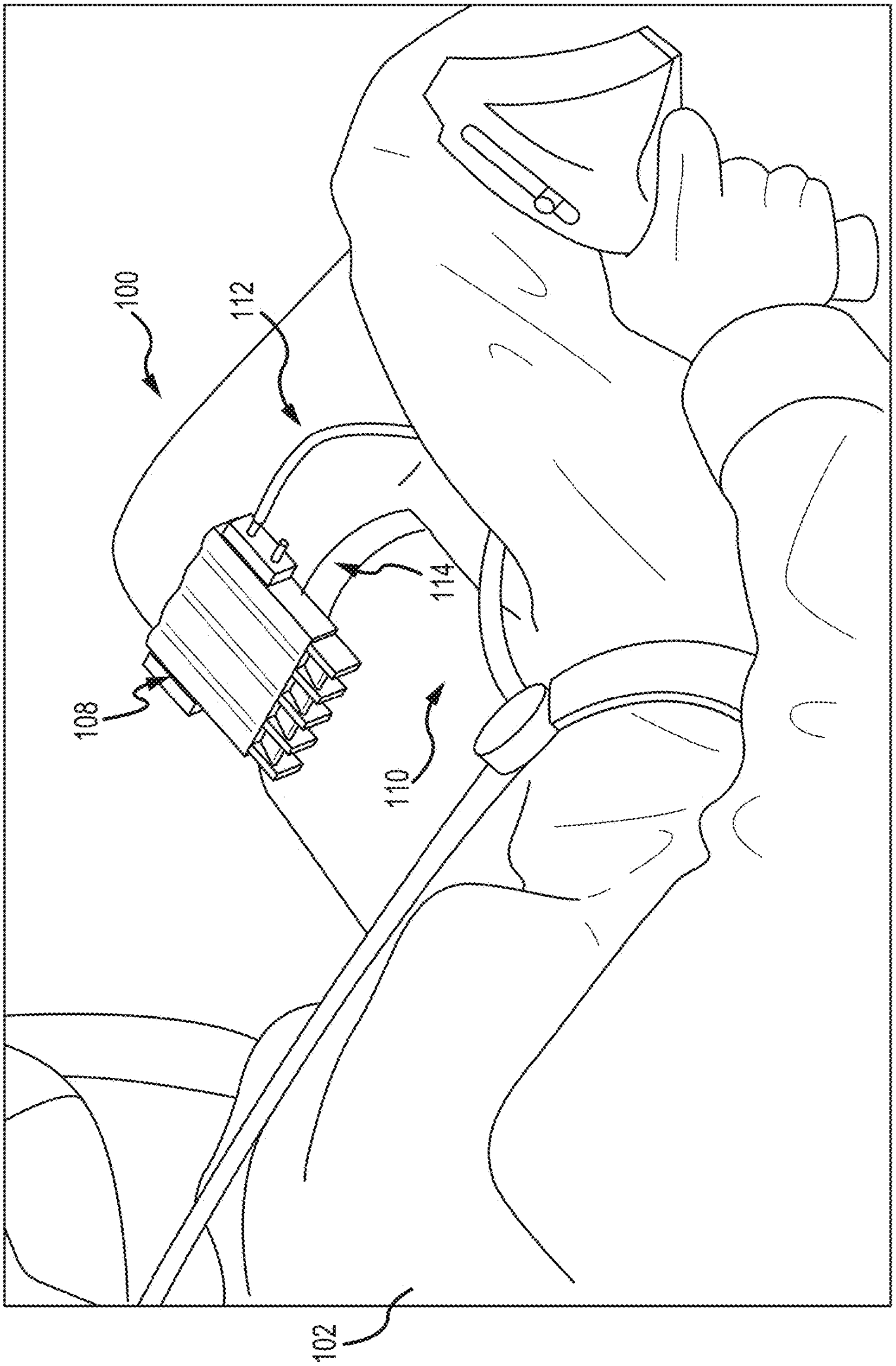
FIGS. 1A and 1B illustrate a urinary relief system, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. While these exemplary embodiments are described in sufficient detail to enable those skilled in the art to practice the invention, it should be understood that other embodiments may be realized and that logical, chemical and mechanical changes may be made without departing from the spirit and scope of the invention. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Disclosed herein is a urinary relief system including a human interface, a storage unit, and a control unit. The human interface is configured to collect and pass a liquid (e.g., urine) from a user (e.g., a pilot) to the storage unit. In various embodiments, the human interface may be designed to be worn under clothing (e.g., flight suit) and close the body of the user. In various embodiments, the huma interface may be fluidly coupled to the storage unit by a hose and, in some embodiments, a quick connector coupling. The storage unit is configured to collect and store the liquid (e.g., urine). In various embodiments, the storage unit includes an absorbent material configured to store the liquid. The various embodiments, the storage unit includes an input fluidly coupled to the human interface device and an output fluidly coupled to the control unit. In various embodiments, the output includes liquid restrictor so that no liquid is passed to the control unit. In various embodiments, the storage unit and the control unit may be coupled by a hose and, in various embodiments, a quick connector coupling.

In various embodiments, the human interface includes a tray, a pad, and an outlet hose. The tray is the apparatus that the user (e.g., the pilot) uses to collect the liquid (e.g., urine). In various embodiments, the tray is designed to fit discreetly and comfortably between the user's undergarments and body. In various embodiments, the human interface is shaped to provide a comfortable fit for the user including a back ridge that allows intuitive positioning of the human interface and a secure seal with the body of the user. In various embodiments, the pad is attached to the tray and is configured to ensure that the human interface is comfortable against the skin of the user. In various embodiments, the pad may include wings that have an adhesive backing to secure the pad, and therefore the human interface, to the undergarments of the user. In various embodiments, the outlet hose is formed into the tray and allows the human interface (e.g., the tray) to be connected to a suction system (e.g., the control unit) to remove the liquid from the tray.

As disclosed herein, the human interface provides a simple, comfortable solution for pilots to relieve themselves (e.g., urinate) during flight. In various embodiments, the human interface disclosed herein does not utilize extensive pre-flight preparations and may be engaged by putting it on/inserting the human interface between the clothing and the body of the user. In various embodiments, as described below, the human interface described herein is smaller than current larger and more expensive solutions. In various embodiments, the human interface described herein may allow for production at a lower cost than currently available systems.

Figure 1B:
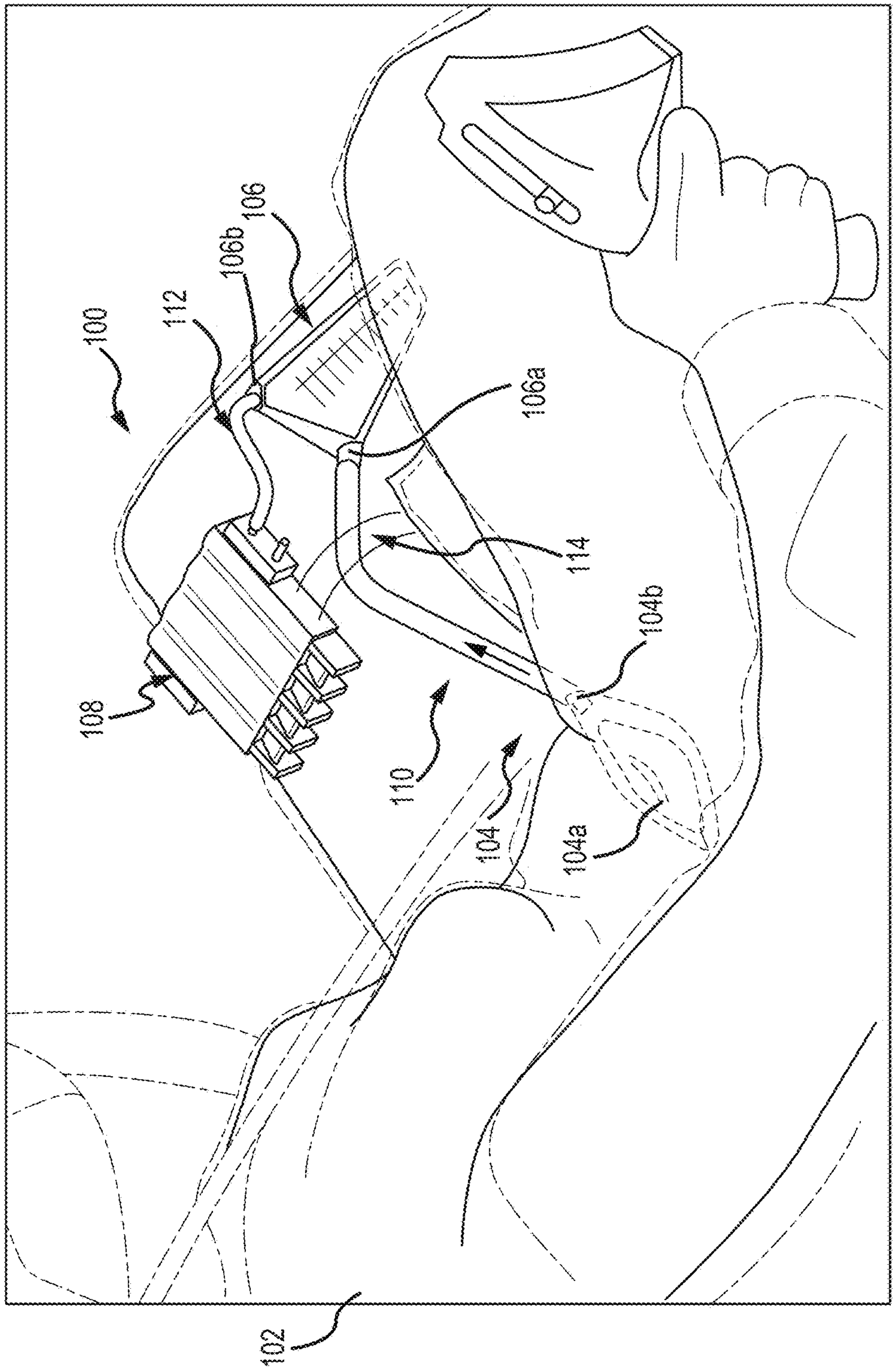

Referring to FIGS. 1A and 1B, a urinary relief system 100 for use by a pilot 102 (e.g., a female pilot) is illustrated, in accordance with various embodiments. Urinary relief system 100 includes a human interface device 104, a storage unit 106, and a control unit 108. Human interface device 104 is configured to be positioned under the clothing (e.g., flight suit, underwear, pants, etc.) and immediately adjacent the body of pilot 102 for use in flight. That is, between the body and clothing of pilot 102 when pilot 102 is in a seated position. In various embodiments, human interface device 104 may form a seal with the body of pilot 102. Human interface device 104 may be any size and/or shape conducive for placement under the clothing of pilot 102 and for collecting the liquid (e.g., urine) while in place. Human interface device 104 includes a collection portion 104*a* and an outlet port 104*b*.

Storage unit 106 includes a storage inlet port 106*a* and a storage outlet port 106*b*. Outlet port 104*b* of human interface device 104 is connected to storage inlet port 106*a* of storage unit 106 by an inlet hose 110 and storage outlet port 106*b* of storage unit 106 is connected to control unit 108 by an outlet hose 112. In various embodiments, storage unit 106 may be disposable. In various embodiments, control unit 108 and/or storage unit 106 may be secured to pilot 102 (e.g., secured to a leg) by one or more straps 114. Storage unit 106 is configured to receive and trap liquid (e.g., urine) received from storage inlet port 106*a* and not allow the liquid to exit through storage outlet port 106*b*.

Control unit 108 creates a motive force that draws the liquid (e.g., urine) from human interface device 104 and into storage unit 106. Air may be drawn, along with the liquid, into storage unit 106 by the vacuum created by control unit 108. In various embodiments, storage unit 106 includes a filter, or flow restrictor, that allows the air to exit storage unit 106 through storage outlet port 106*b* and keep the liquid secured in storage unit 106. In various embodiments, storage unit 106 contains a gelling agent to convert inflowing liquids to solids, lowering risk of leakage. In various embodiments, control unit 108 provides the motive force by creating a vacuum to draw the liquid from human interface device 104 to storage unit 106.

Figure 2:
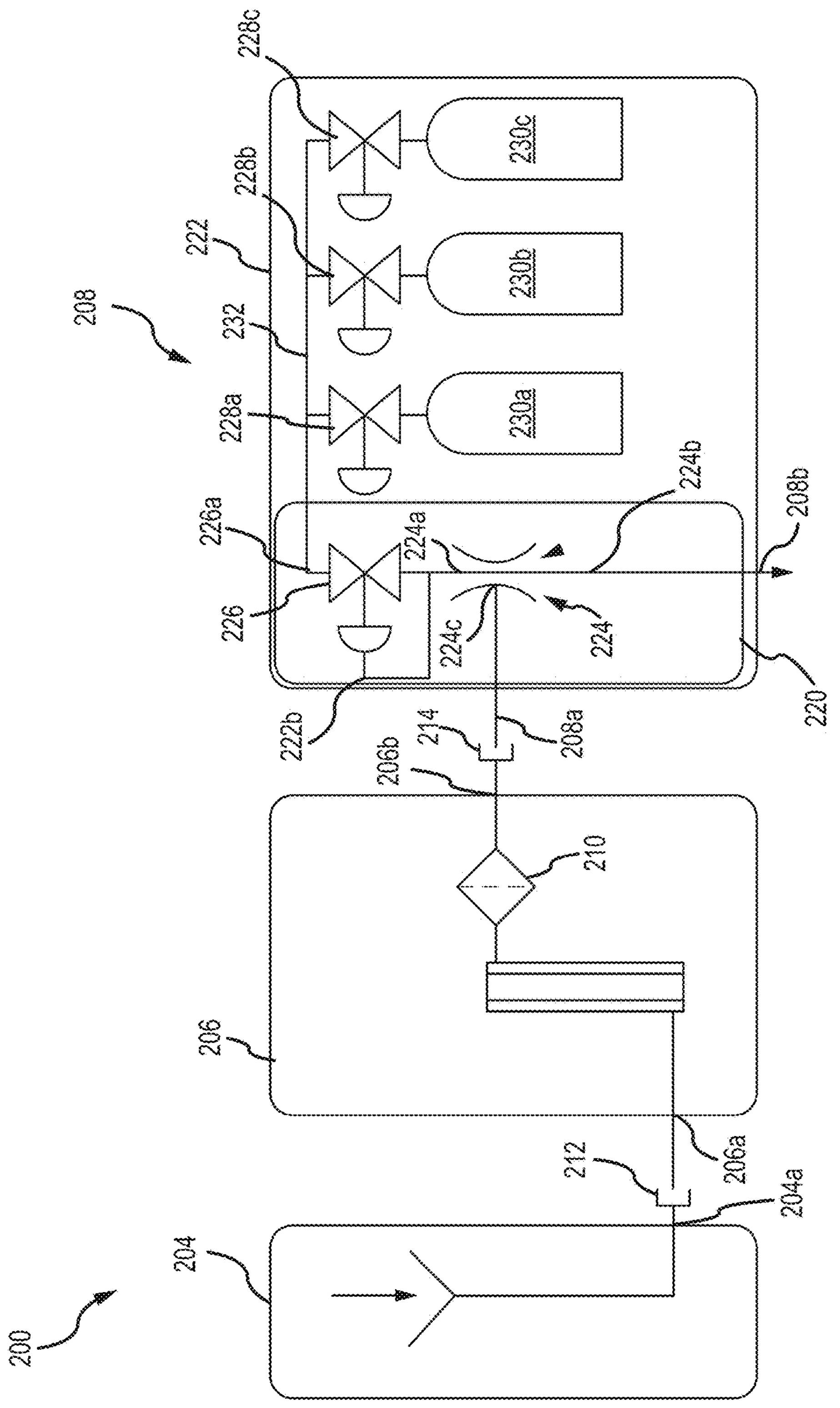
FIG. 2 illustrates a functional diagram of a urinary relief system, in accordance with various embodiments.

Referring now to FIG. 2, a functional diagram 200 of a urinary relief system is illustrated, in accordance with various embodiments. Functional diagram 200 may be an example of urinary relief system 100 described above with respect to FIGS. 1A and 1B. Functional diagram 200 includes a collection device 204, a storage device 206, and a control device 208. In various embodiments, collection device 204, storage device 206, and control device 208 may be examples of human interface device 104, storage unit 106, and control unit 108, respectively, described above with respect to FIGS. 1A and 1B.

Collection device 204 is configured to collect liquid (e.g., urine) from a user (e.g., pilot 102). Collection device 204 has an outlet port 204*a*, storage device 206 has a storage inlet port 206*a* and a storage outlet port 206*b*, and control device 208 has a control inlet port 208*a* and a control outlet port 208*b*. Outlet port 204*a* of collection device 204 is configured to transfer the collected liquid from collection device 204 to storage device 206. Outlet port 204*a* of collection device 204 is connected to storage inlet port 206*a* of storage device 206. Storage outlet port 206*b* of storage device 206 is connected to control inlet port 208*a* of control device 208. In various embodiments, a hose, or tube, may be used to make the connection between outlet and inlet ports. In various embodiments, there is a first quick connector interface 212 between collection device 204 and storage device 206 that allows for quick and simple attachment and detachment of a hose, or tube. In various embodiments, there is a second quick connector interface 214 between storage device 206 and control device 208 that allows for quick and simple attachment and detachment of the hose, or tube. In various embodiments, a filter, or flow restrictor 210, is connected to storage outlet port 206*b* of storage device 206. Flow restrictor 210 prevents liquid (e.g., urine) from passing to control device 208 while allowing air to pass to control device 208.

Control device 208 includes an ejector head 220 and a pressurized gas supply 222. Ejector head 220 includes houses control inlet port 208*a*, control outlet port 208*b*, an ejector 224, and a pressure regulator 226. Ejector 224 is coupled to pressure regulator 226, control inlet port 208*a*, and control outlet port 208*b*. Pressurized gas supply 222 includes a first valve 228*a*, a second valve 228*b*, a third valve 228*c*, a first $CO_2$ cartridge 230*a*, a second $CO_2$ cartridge 230*b*, and a third $CO_2$ cartridge 230*c*. First $CO_2$ cartridge 230*a* is coupled to first valve 228*a*, second $CO_2$ cartridge 230*b* is coupled to second valve 228*b*, and third $CO_2$ cartridge 230*c* is coupled to third valve 228*c*. First valve 228*a*, second valve 228*b*, and third valve 228*c* are connected in parallel to pressure regulator 226 by a high pressure line 232. That is, each valve 228*a*, 228*b*, 228*c* has an independent high pressure connection to high pressure line 232 that is in turn connected to pressure regulator 226. While the description herein uses $CO_2$ cartridges, it should be appreciated that any suitable pressurized gas container may be used.

Each $CO_2$ cartridge 230*a*, 230*b*, 230*c* is sealed and connected to the corresponding valve 228*a*, 228*b*, 228*c*. Each valve 228*a*, 228*b*, 228*c* performs the same function. For example, first valve 228*a* is configured to puncture the seal of first $CO_2$ cartridge 230*a*, in response to an input, allowing the compressed air in first $CO_2$ cartridge 230*a* to pass through first valve 228*a*, into high pressure line 232, and to pressure regulator 226. Second valve 228*b* is configured to puncture the seal of second $CO_2$ cartridge 230*b*, in response to an input, allowing the compressed air in second $CO_2$ cartridge 230*b* to pass through second valve 228*b*, into high pressure line 232, and to pressure regulator 226. Third valve 228*c* is configured to puncture the seal of third $CO_2$ cartridge 230*c*, in response to an input, allowing the compressed air in third $CO_2$ cartridge 230*c* to pass through third valve 228*c*, into high pressure line 232, and to pressure regulator 226.

Pressure regulator 226 has a high pressure inlet 226*a* and a reduced pressure outlet 226*b*. Pressure regulator 226 receives the high pressure air from high pressure line 232 at high pressure inlet 226*a*, reduces the pressure of the air (e.g., $CO_2$), and outputs the air at a reduced pressure from reduced pressure outlet 226*b*. The pressure of the air at reduced pressure outlet 226*b* is about 15 times to about 45 times less than the pressure of the air received at high pressure inlet 226*a*. In various embodiments, the pressure of the air at reduced pressure outlet 226*b* is about 25 times to about 35 times less than the pressure of the air received at high pressure inlet 226*a*. Reducing the pressure of the air by pressure regulator 226 slows the release of the pressurized air (e.g., $CO_2$) and therefore extends the lifespan of each $CO_2$ cartridge 230*a*, 230*b*, 230*c*. Adjusting the release pressure (e.g., air pressure at reduced pressure outlet 226*b*) either up or down may decrease or increase, respectively, the effective lifespan of each $CO_2$ cartridge 230*a*, 230*b*, 230*c*.

Ejector 224 has an air inlet 224*a*, an air outlet 224*b*, and a vacuum port 224*c*. Air inlet 224*a* of ejector 224 is connected to reduced pressure outlet 226*b* of pressure regulator 226. Air outlet 224*b* is connected to control outlet port 208*b* which is open to the environment (e.g., cockpit, cabin, etc.). Vacuum port 224*c* is connected to storage outlet port 206*b* of storage device 206. Ejector 224 receives pressurized air at air inlet 224*a* and passes the pressurized air to air outlet 224*b* to create a vacuum at vacuum port 224*c*. The vacuum creates a motive force that passes through storage device 206 to collection device 204 and draws, or sucks, air and liquid (e.g., urine) from collection device 204 into storage device 206. A combination of the materials inside storage device 206 and flow restrictor 210 trap and prevent the liquid from being pulled to ejector head 220, and more specifically, into ejector 224. Instead, any air present in the system is drawn by the vacuum created by ejector 224, continuing to pull liquid from collection device 204.

Figure 3B:
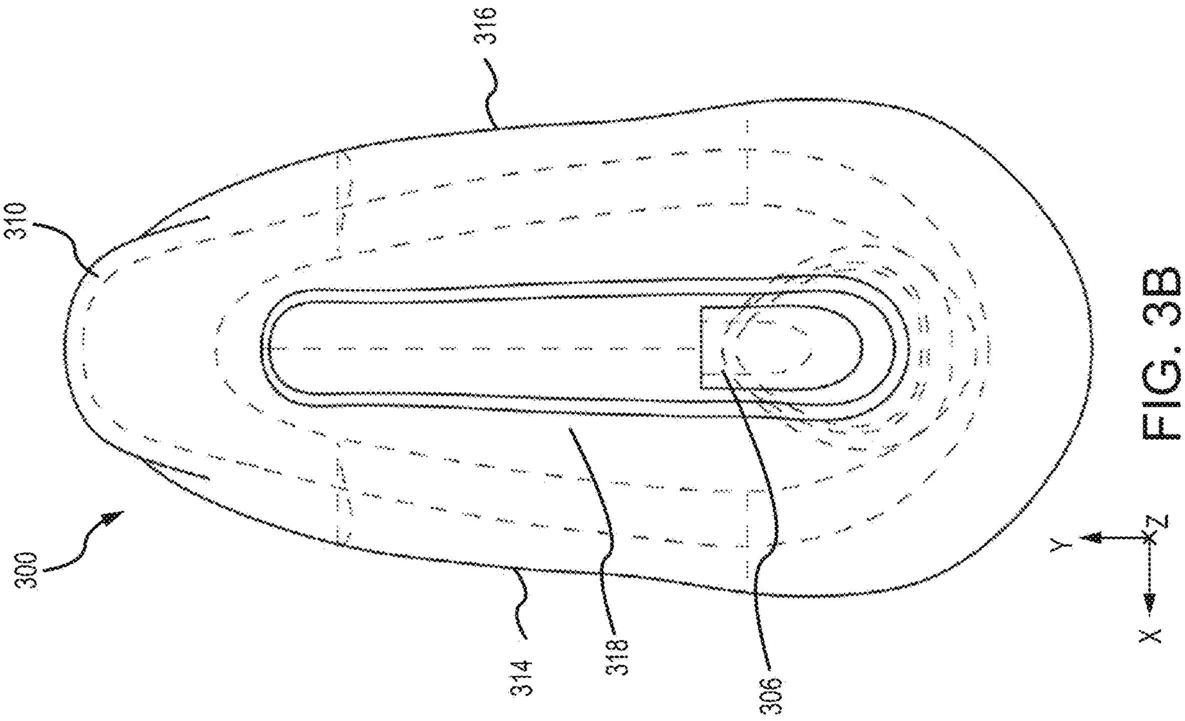
FIGS. 3A, 3B, 3C, 3D, 3E, 3F, 3G, 3H, 3I, and 3J illustrate a human interface device for use with a urinary relief system, in accordance with various embodiments.
Figure 3A:
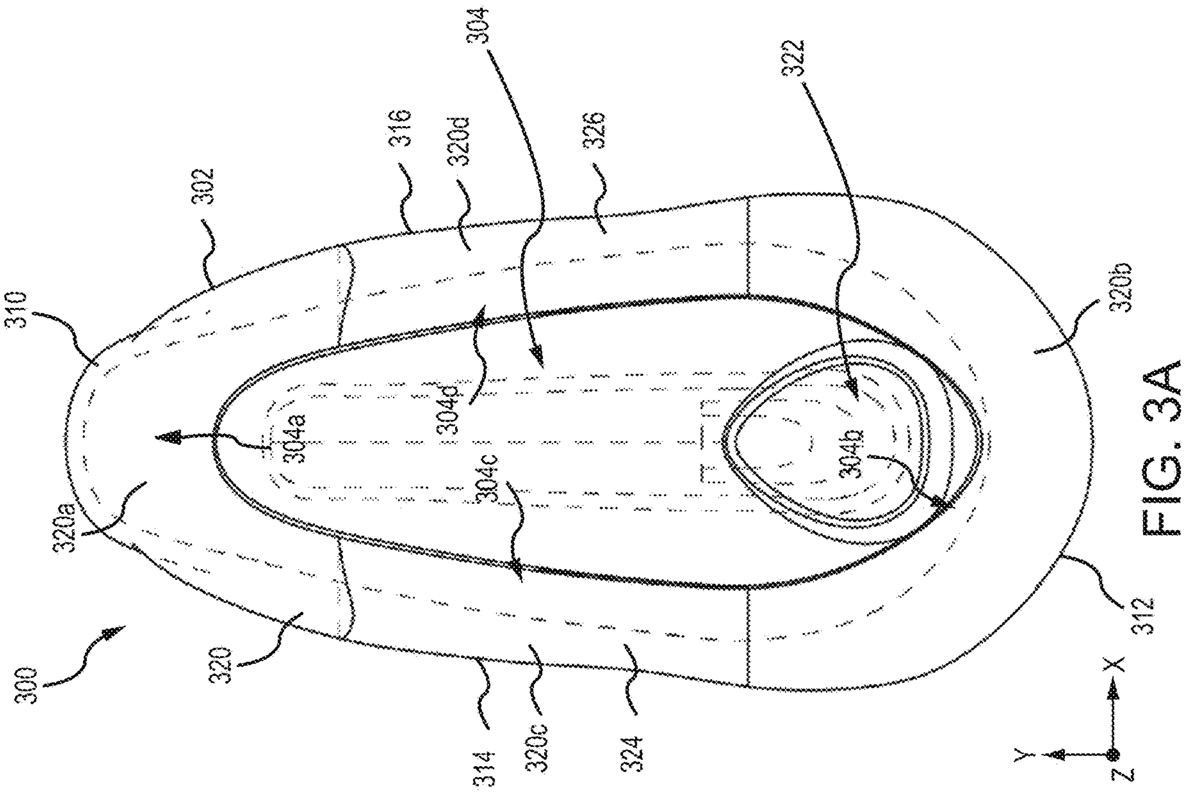
Figure 3D:
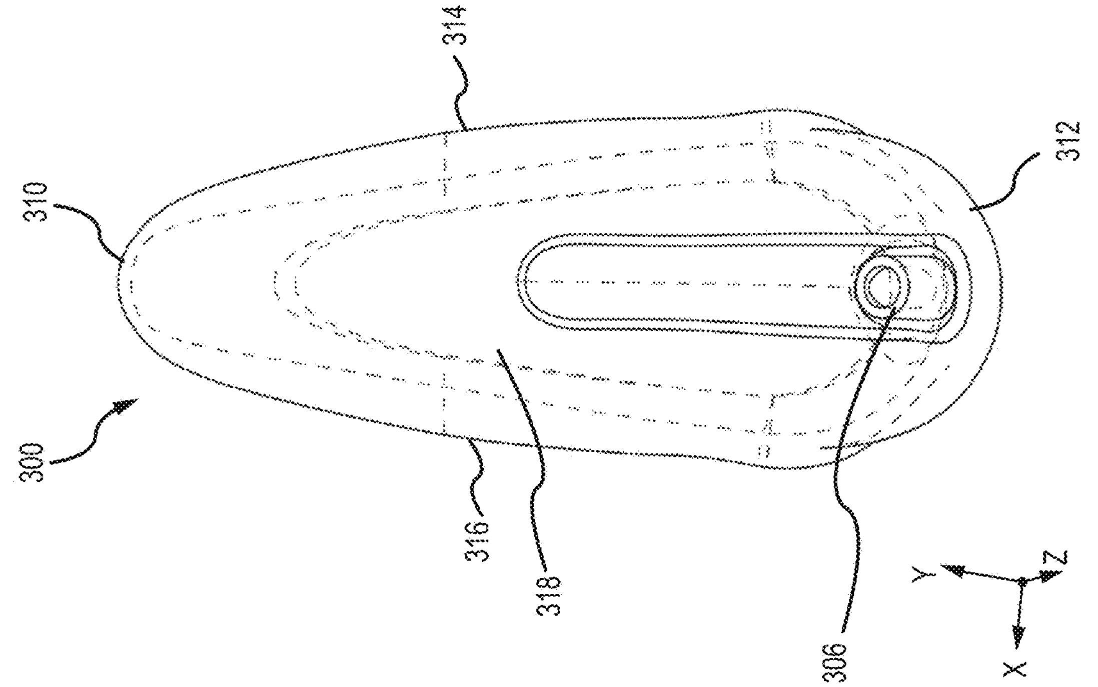
Figure 3C:
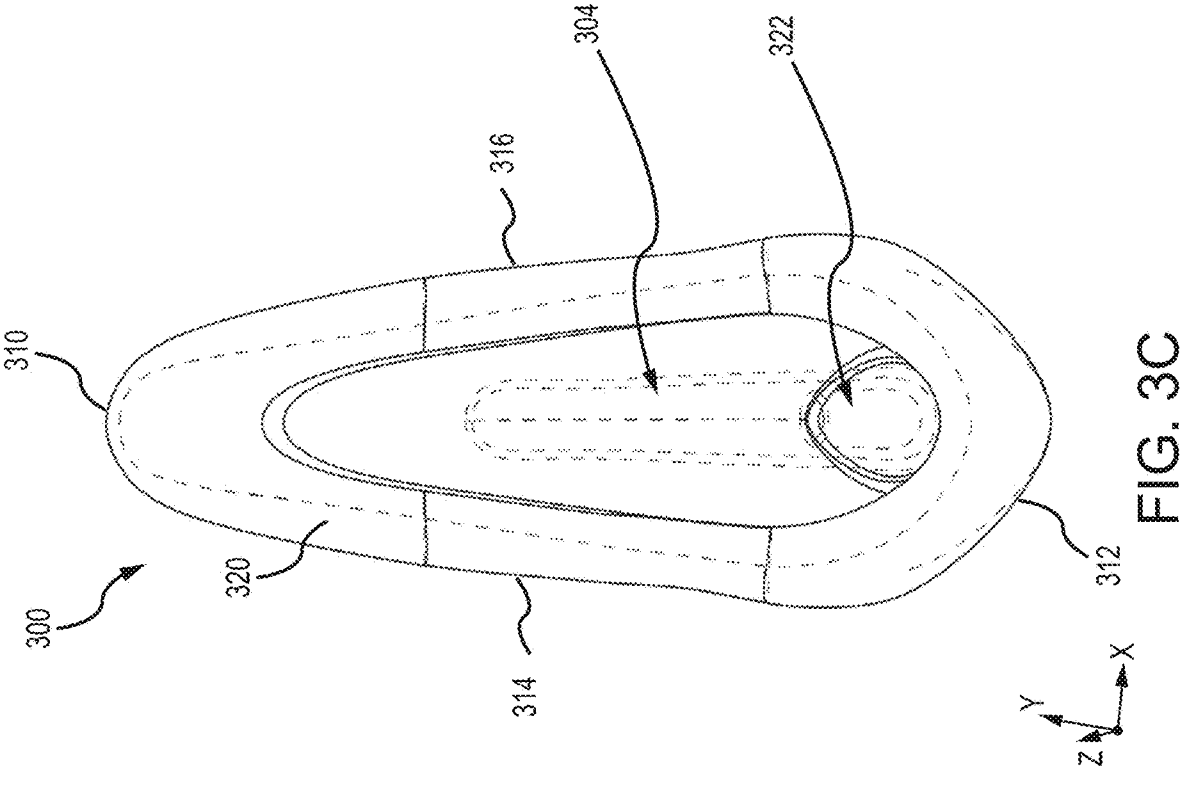
Figure 3G:
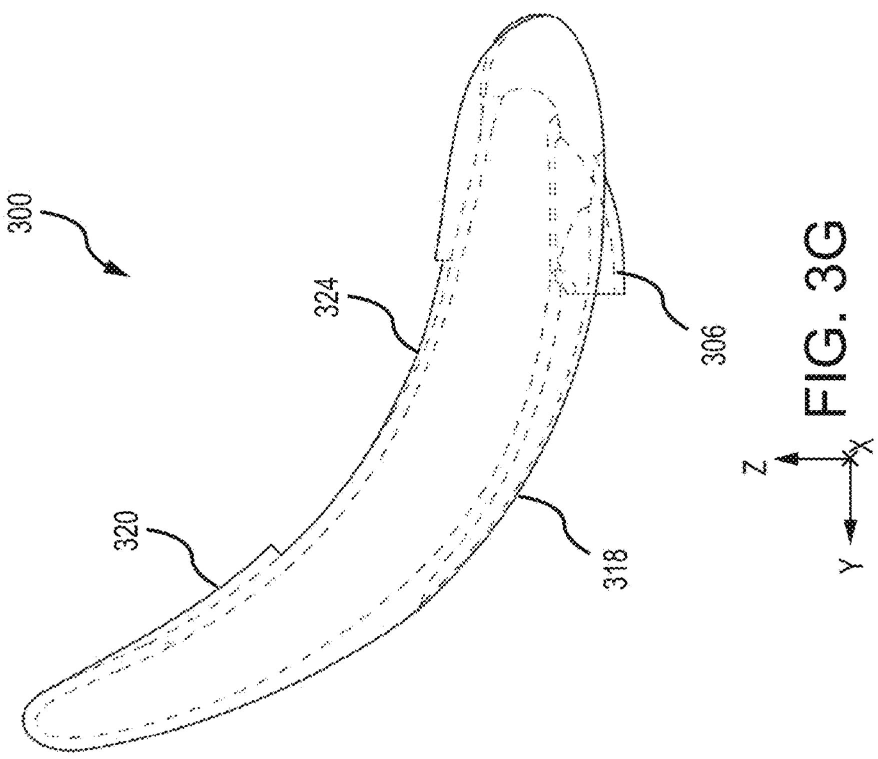
Figure 3F:
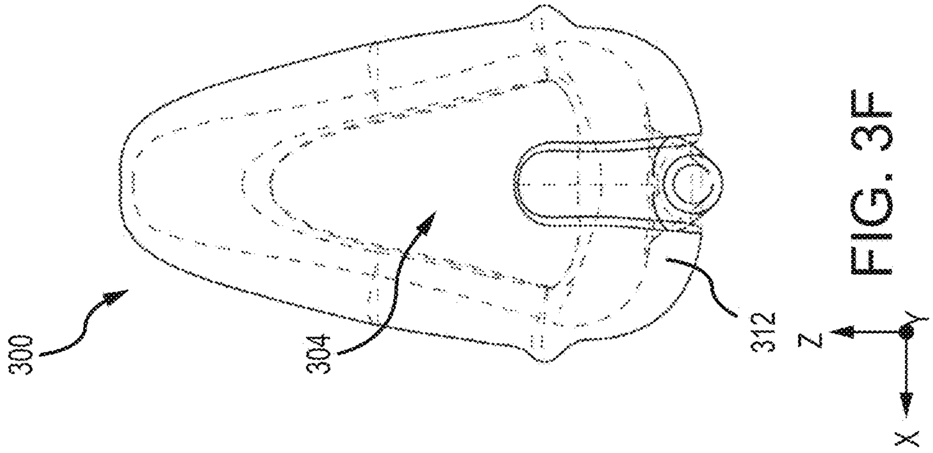
Figure 3E:
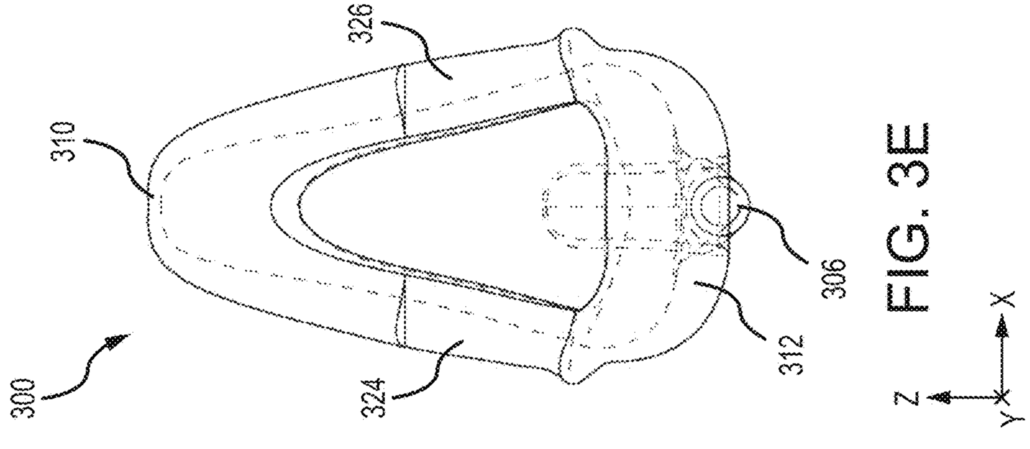
Figure 3J:
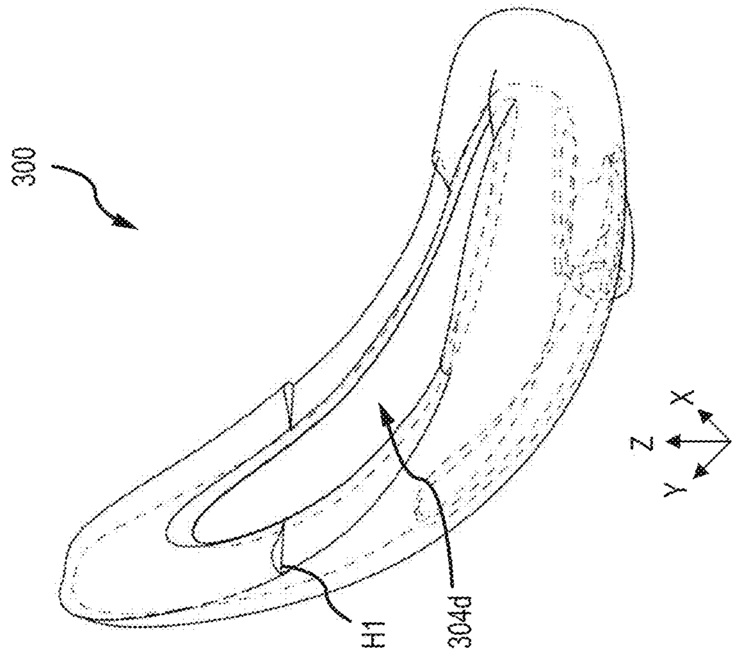
Figure 3I:
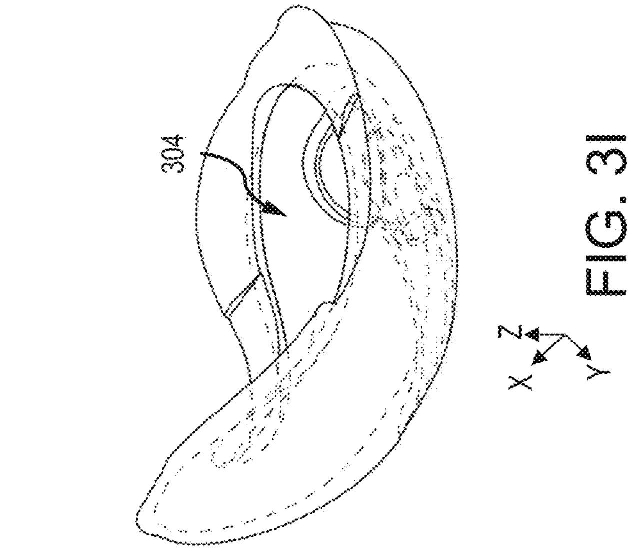
Figure 3H:
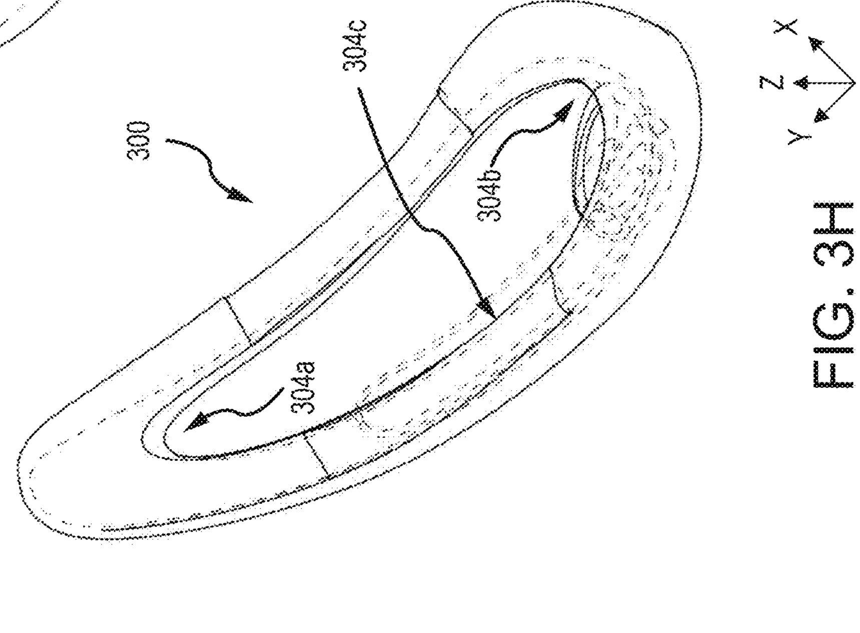

Referring now to FIGS. 3A-3J, a human interface device 300 is illustrated, in accordance with various embodiments. In various embodiments, human interface device 300 may be an example of human interface device 104 described above with respect to FIGS. 1A and 1B. In various embodiments, human interface device 300 may be an example of collection device 204 described above with respect to FIG. 2. FIG. 3A illustrates a top view of human interface device 300, FIG. 3B illustrates a bottom view of human interface device 300, FIG. 3C illustrates of a perspective top view of human interface device 300, FIG. 3D illustrates a perspective bottom view of human interface device 300, FIG. 3E illustrates a back view of human interface device 300, FIG. 3F illustrates a front view of human interface device 300, FIG. 3G illustrates a side view of human interface device 300, FIG. 3H illustrates an isometric north-east view (e.g., from a viewpoint rotated 225° and tilted 45° from center) of human interface device 300, FIG. 3I illustrates an isometric south-east view (e.g., from a viewpoint rotated 315° and tilted 45° from center) of human interface device 300, and FIG. 3J illustrates a perspective side view of human interface device 300.

Human interface device 300 includes a body 302, a fluid cavity 304 defined by body 302, and an outlet 306 extending from fluid cavity 304 through body 302. Body 302 has a front 310, a back 312, a first side 314, a second side 316, a bottom 318, and a top 320. Fluid cavity 304 is defined by the front 310, back 312, first side 314, second side 316, and bottom 318. Top 320 has an opening through which fluid (e.g., urine) enters fluid cavity 304. Fluid cavity 304 includes a funnel 322 that connects fluid cavity 304 to outlet 306. Outlet 306 is centered between first side 314 and second side 316 and located near back 312 of body 302. Outlet 306 extends toward front 310 of body 302, having an opening toward front 310. Fluid enters fluid cavity 304 through top 320 that is open, flows from fluid cavity 304 into funnel 322, and out of human interface device 300 through outlet 306. In various embodiments, outlet 306 is fluidly coupled to a storage unit (e.g., storage device 206) by a hose, a tube, or other mechanism. In various embodiments, different motive forces (e.g., vacuum as described above with respect to FIG. 2) may transfer the liquid from human interface device 300, specifically through outlet 306, to the storage unit.

Human interface device 300 is configured to be worn by aircrew (e.g., pilot 102) while in a seated position. Accordingly, funnel 322 and outlet 306 are near back 312 of body 302 as body 302 will be tilted toward back 312 while the aircrew is seated. This allows the liquid in fluid cavity 304 to move toward funnel 322 to be evacuated, during normal flight operations. Top 320 has a front portion 320*a*, a back portion 320*b*, a first side portion 320*c*, and a second side portion 320*d*, corresponding to front 310, back 312, first side 314, and second side 316, respectively. Front portion 320*a* has a larger surface area than back portion 320*b*. Front 310 of body 302 may be used by the aircrew to adjust the position of human interface device 300 while in use. First side 314 and second side 316, including first side portion 320*c* and second side portion 320*d* of top 320, are curved inward (e.g., along the x-axis) between front 310 and back 312. This curve allows body 302 to contour to the body of the aircrew and accommodate the legs of the aircrew while human interface device 300 is in use. Additionally, body 302 has a curve upward (e.g., in the positive z-direction) from back 312 to front 310, to accommodate the anatomy of the user and provide a better fit.

Top 320 overhangs fluid cavity 304, forming a lip over fluid cavity 304. Fluid cavity 304 has a front portion 304*a*, a back portion 304*b*, a first side portion 304*c*, and a second side portion 304*d*. Front portion 304*a* of fluid cavity 304 is located under front portion 320*a* of top 320, back portion 304*b* is located over funnel 322 and over back portion 320*b*, first side portion 304*c* is located under first side portion 320*c* of top 320, and second side portion 304*d* is located under second side portion 320*d* of top 320. Fluid cavity is configured to receive and move liquid (e.g., urine) toward funnel 322 and ultimately out through outlet 306.

Top 320 further includes a first indent 324 along first side portion 320*c* and a second indent 326 along second side portion 320*d*. First and second indents 324, 326 are shorter (e.g., along the z-direction) than the remainder of top 320. The surface of first and second indents 324, 326 extend from an interior (e.g., adjacent fluid cavity 304) to an exterior (e.g., opposite fluid cavity 304) of top 320. That is, first indent 324 extends from fluid cavity 304 toward an exterior surface of first side 314 (e.g., in the positive x-direction) and second indent extends from fluid cavity 304 to an exterior surface of second side 316 (e.g., in the negative x-direction). Top 320 extends above indents 324, 326 by a height H1. In various embodiments, height H1 is uniform in both the x-direction and the y-direction. In various embodiments, height H1 varies in the x-direction. That is, top surface may be contoured, or sloped, from an exterior side to an interior side for better ergonomics and comfort.

Human interface device 300 may be formed as a single monolithic component such that all components of body 302 are formed together. In various embodiments, top 320 may be formed independent of the remainder of body 302 and coupled to body 302. Body 302 may be formed of a material that is flexible, and in various embodiments skin-safe, while maintaining its shape, such as plastic, rubber, vinyl, polyurethane, polylactic acid (PLA), acrylonitrile butadiene styrene (ABS), or silicone, among others. In various embodiments, body 302 may become more flexible in response to the heat from the body of the user while in use.

Figure 4C:
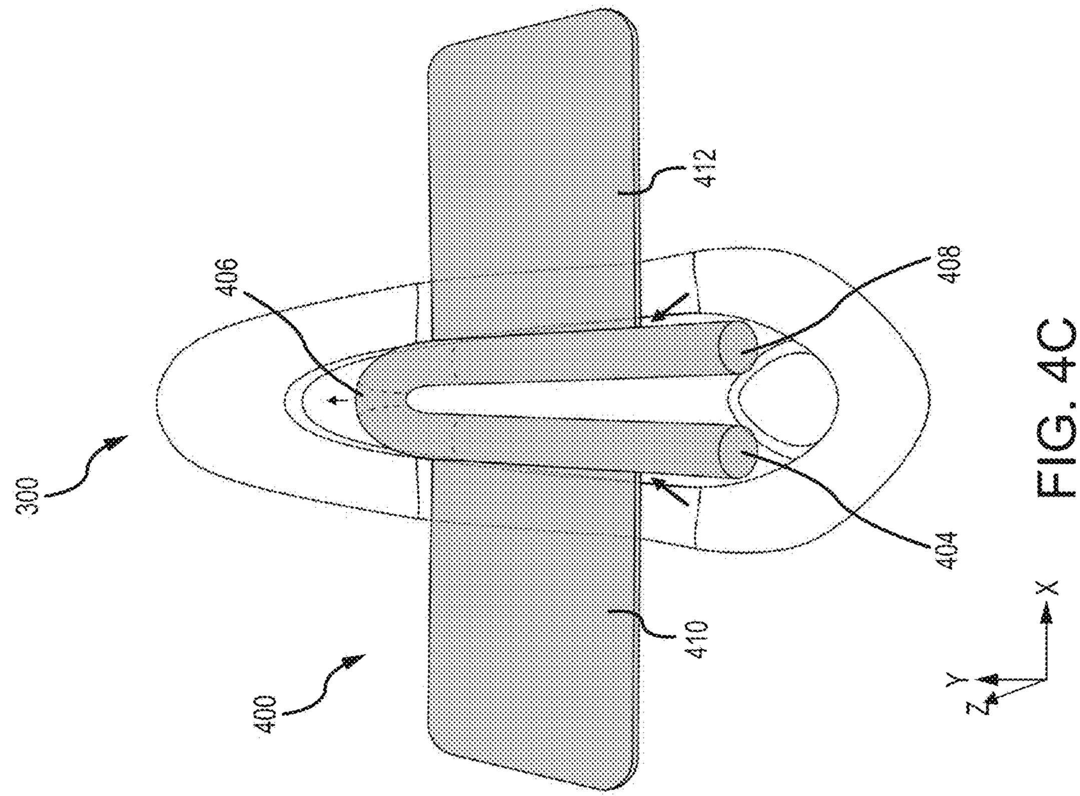
FIGS. 4A, 4B, and 4C illustrate a pad for use with a human interface device in a urinary relief system, in accordance with various embodiments.
Figure 4A:
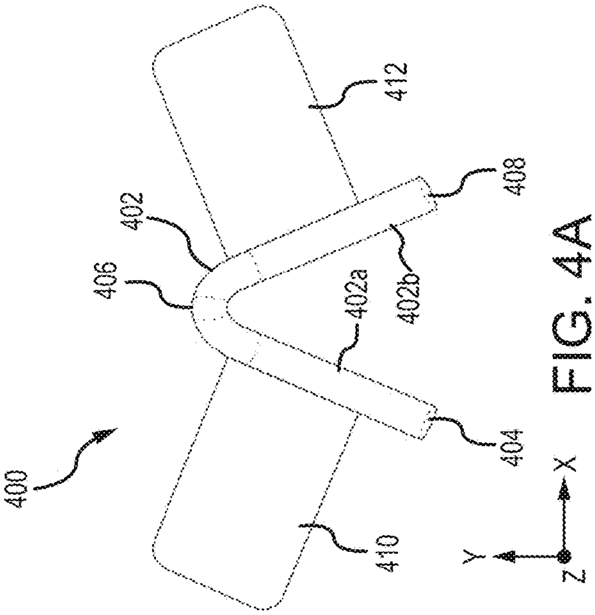
Figure 4B:
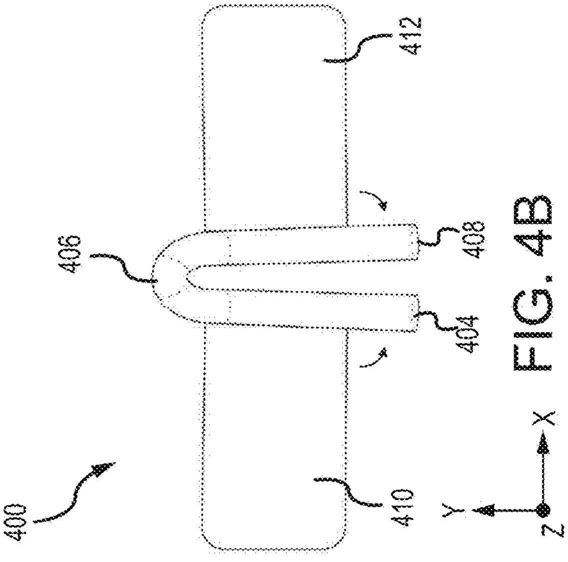

Referring now to FIGS. 4A-4C, a pad 400 for use with human interface device 300 is illustrated, in accordance with various embodiments. FIGS. 4A and 4B illustrate pad 400 and FIG. 4C illustrates pad 400 being inserted into human interface device 300. Pad 400 has a body 402 having a linear shape including a first portion 402*a*, a second portion 402*b*, a first end 404, a mid-point 406, and a second end 408. First portion 402*a* extends from first end 404 to mid-point 406 and second portion 402*b* extends from mid-point 406 to second end 408. Body 402 is tubular in shape extending from first end 404 to second end 408. In various embodiments, body 402 has a circular cross section so that body 402 is cylindrical in shape. In various embodiments, the cross section of body 402 may pentagonal, hexagonal, or any other shape. Body 402 is configured bend around mid-point 406 as illustrated in FIGS. 4A-4C.

Pad 400 further includes a first wing 410 and a second wing 412. First wing 410 connects to body 402 between first end 404 and mid-point 406 and extends outward from body 402 in a first direction (e.g., in the negative x-direction as illustrated in FIG. 4B). Second wing 412 connects to body 402 between mid-point 406 and second end 408 and extends outward from body 402 in a second direction (e.g., in the positive x-direction as illustrated in FIG. 4B). The first direction and the second direction may both be the same direction before body 402 is bent, or folded, about mid-point 406. In use, the first direction and the second direction may not exactly opposite as illustrated in FIG. 4B, but may offset in different directions (e.g., FIG. 4A).

Pad 400 is configured to be inserted into human interface device 300, and more specifically, inserted into fluid cavity 304 as illustrated in FIG. 4C. That is, pad 400 may be folded, or bent, and inserted in fluid cavity 304 so that mid-point 406 is adjacent front 310 and first end 404 and second end 408 are adjacent back 312. Depending on user preference, pad 400 may be moved more forward toward front 310, including into front portion 304*a* of fluid cavity under top 320. First portion 402*a* may be inserted under top 320, and more specifically, under first side portion 320*c* of top 320 and into first side portion 304*c*. Second portion 402*b* may be inserted under top 320, and more specifically, under second side portion 320*d* of top 320 and into second side portion 304*d*. First wing 410 is configured to fit within first indent 324 and second wing 412 is configured to fit within second indent 326.

Pad 400 may be made from materials that are softer than human interface device 300 to provide improved comfort during use. First wing 410 and second wing 412 help secure pad 400 to human interface device 300 and to the user (e.g., pilot 102). In various embodiments, first wing 410 and second wing 412 help secure pad 400 to the underwear of the user to ensure that human interface device 300 does not move during use. In various embodiments, pad 400 may be made from an absorbent material such as wood pulp, cellulose, sodium polyacrylate, and/or polyacrylamide hydrogel, among others. In various embodiments, pad 400 may be made from less absorbent materials. When inserted into human interface device 300, pad 400 reduces liquid splash back during use of human interface device 300. In various embodiments, pad 400 may reduce the size of the opening in top 320 which users have indicated as being more comfortable to use than a larger opening.

Figure 5:
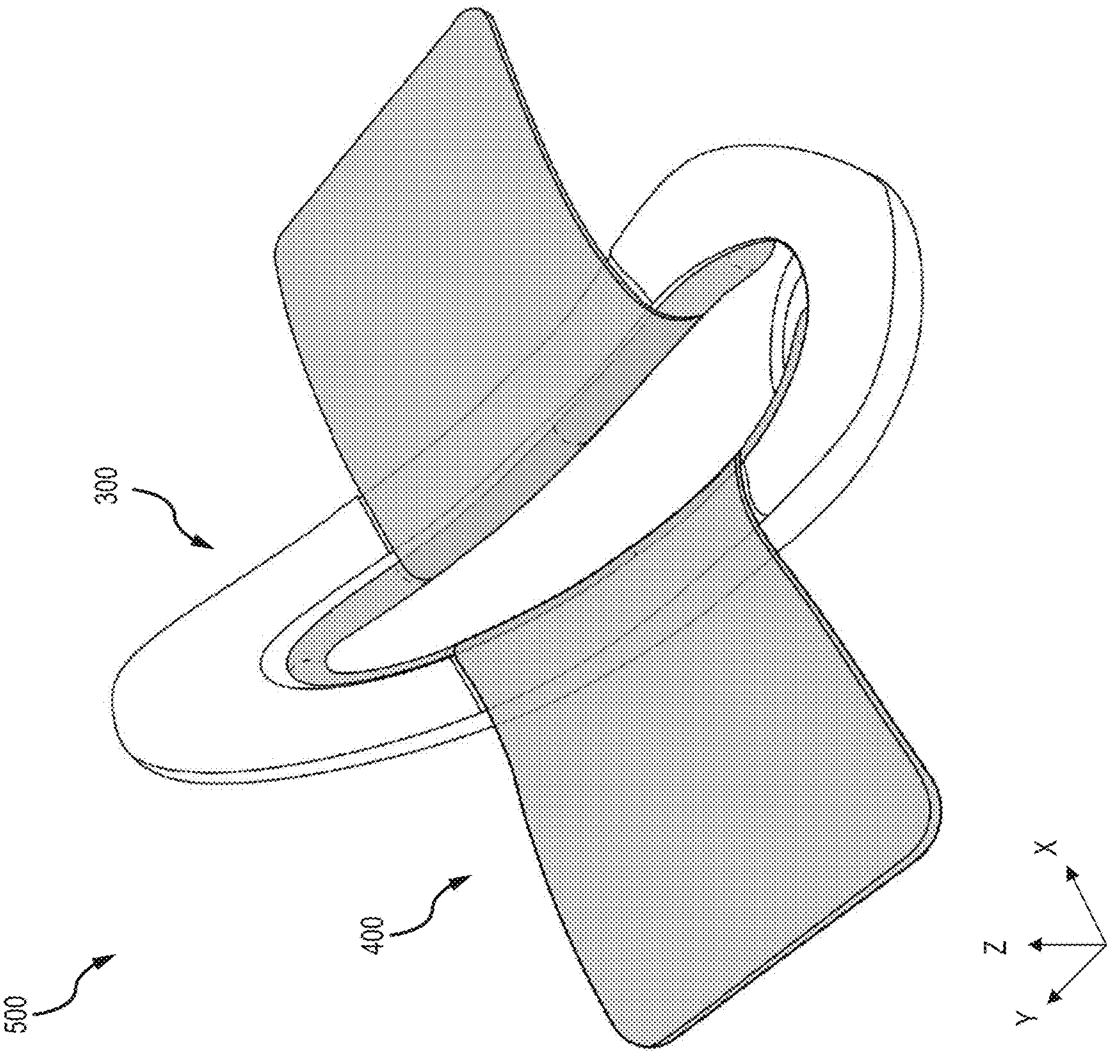
FIG. 5 illustrates an assembled pad and human interface device for use with a urinary relief system, in accordance with various embodiments.

Referring now to FIG. 5, a human interface assembly 500 including human interface device 300 and pad 400 is illustrated, in accordance with various embodiments. As described above, pad 400 is inserted into human interface device 300 to improve comfort (e.g., pad 400 using softer material than human interface device 300), reduce liquid splash back during use, secure human interface device 300 to the user, and to keep user dry during use, among other benefits. In various embodiments, first wing 410 and second wing 412 may include a first adhesive to secure first wing 410 to first indent 324 and second wing 412 to second indent 326. In various embodiments, first wing 410 and second wing 412 may include a second adhesive to secure first wing 410 and second wing 412 to the user (e.g., the garments and/or underwear of the user).

Referring now to FIGS. 6A-6M, a human interface device 600 is illustrated, in accordance with various embodiments. In various embodiments, human interface device 600 may be an example of human interface device 104 described above with respect to FIGS. 1A and 1B. In various embodiments, human interface device 600 may be an example of collection device 204 described above with respect to FIG. 2.

Figure 6B:
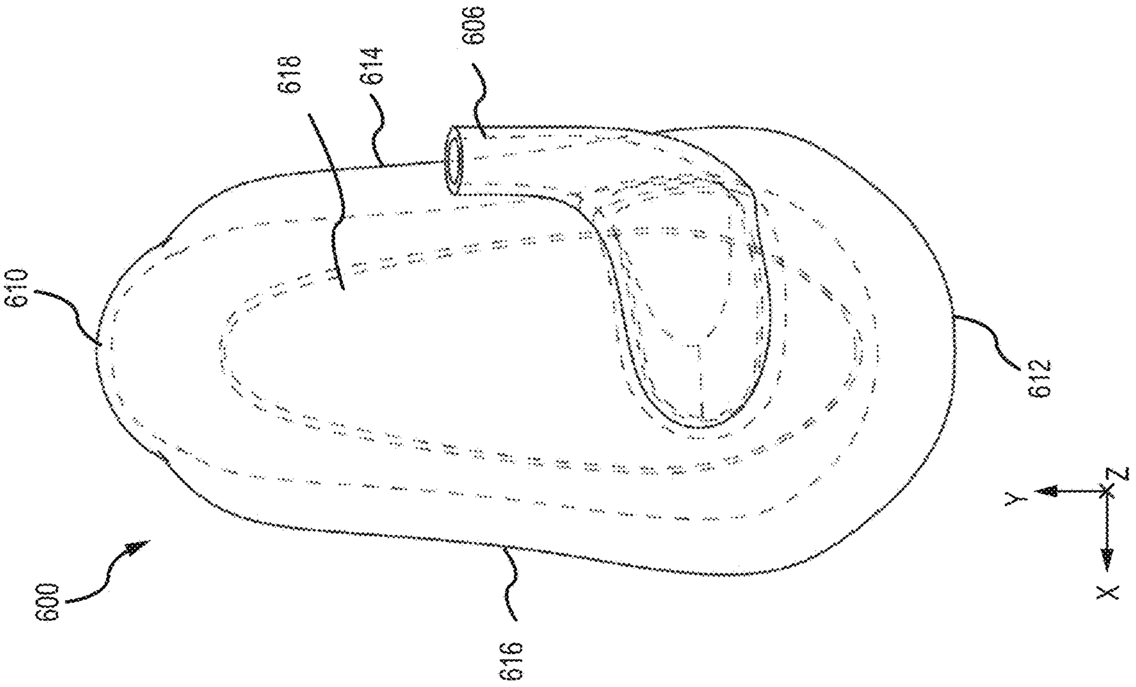
FIGS. 6A, 6B, 6C, 6D, 6E, 6F, 6G, 6H, 6I, 6J, 6K, 6L, and 6M illustrate a human interface device for use with a urinary relief system, in accordance with various embodiments.
Figure 6A:
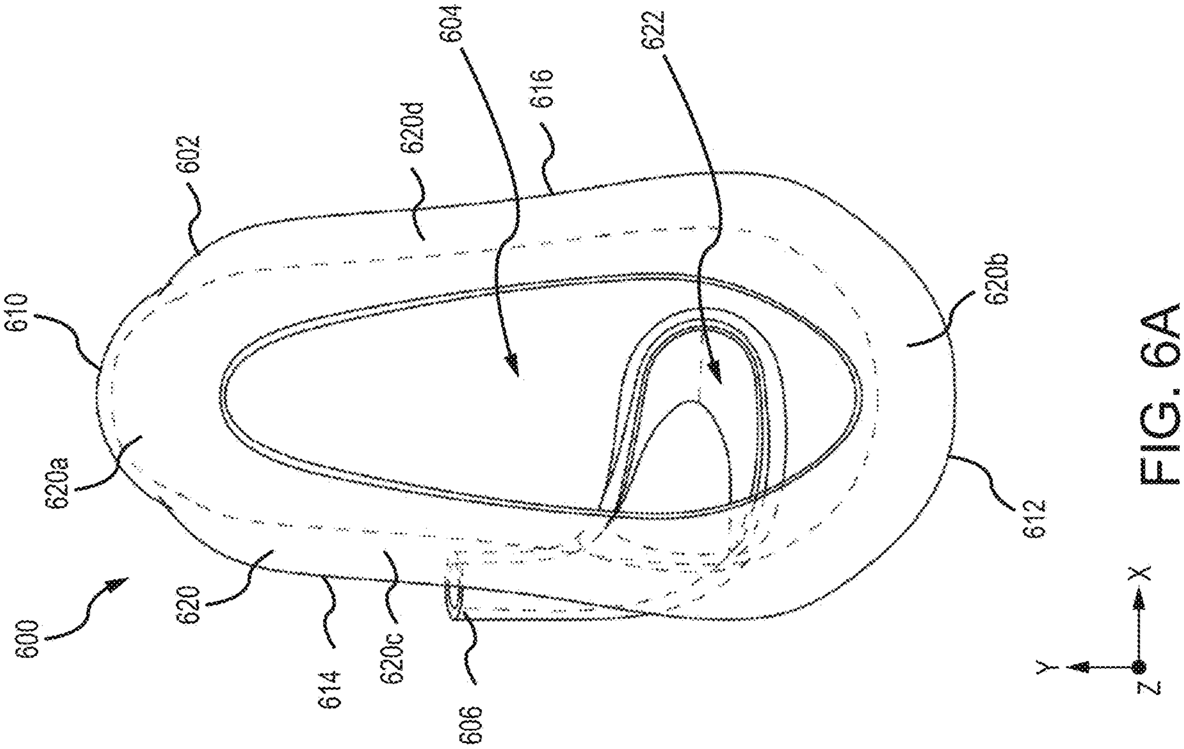
Figure 6D:
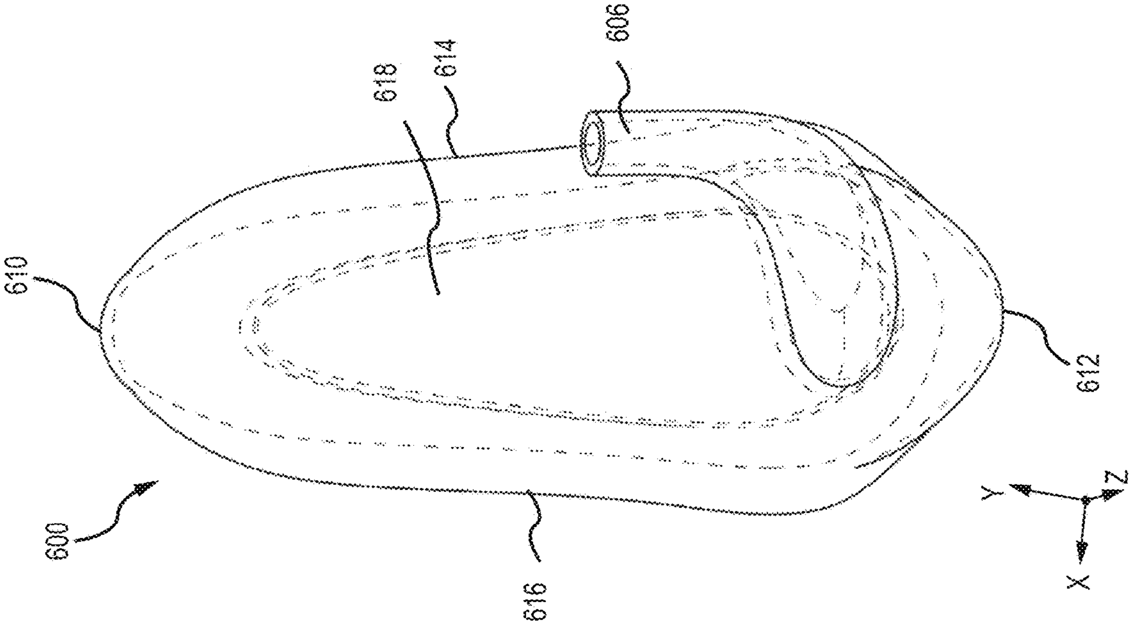
Figure 6C:
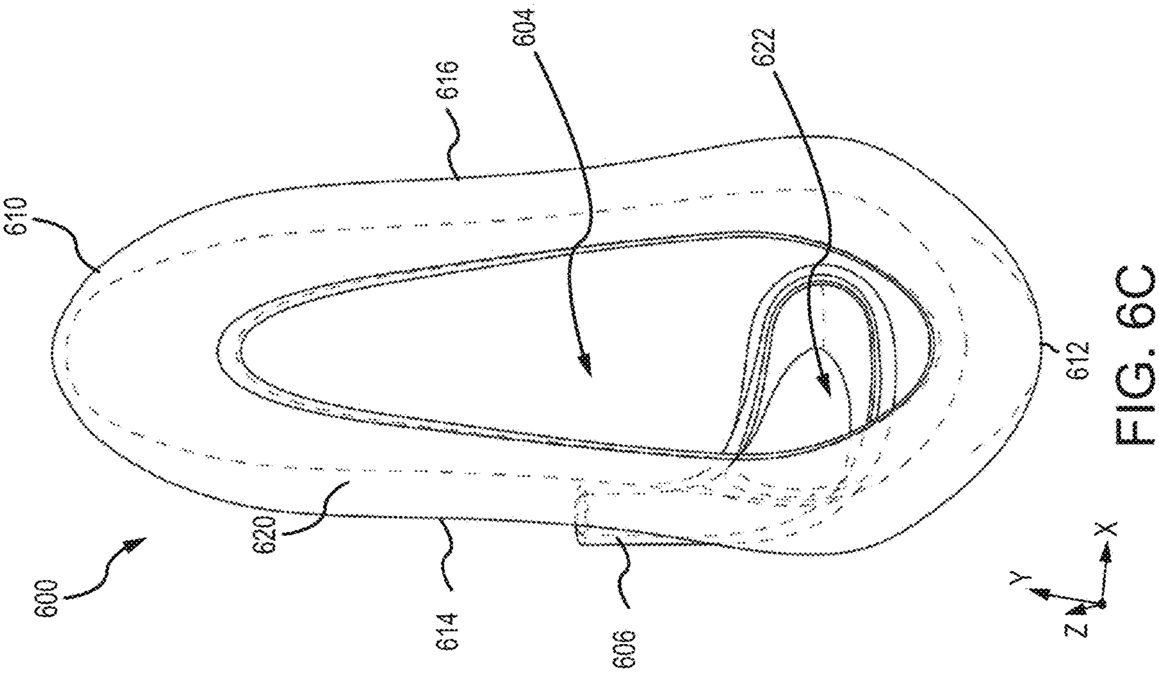
Figure 6G:
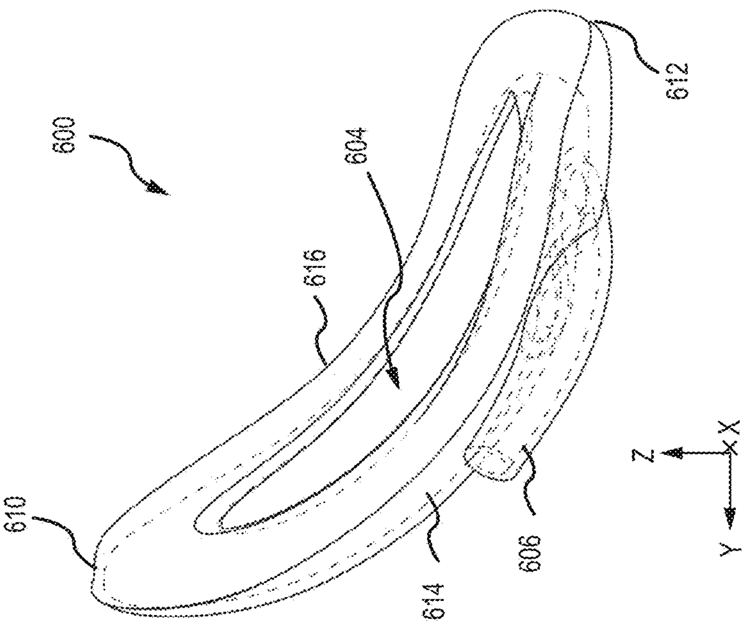
Figure 6F:
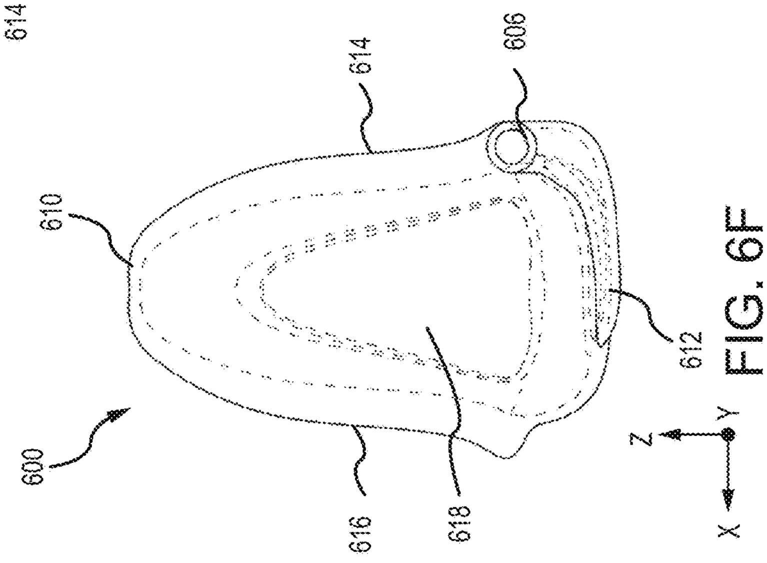
Figure 6E:
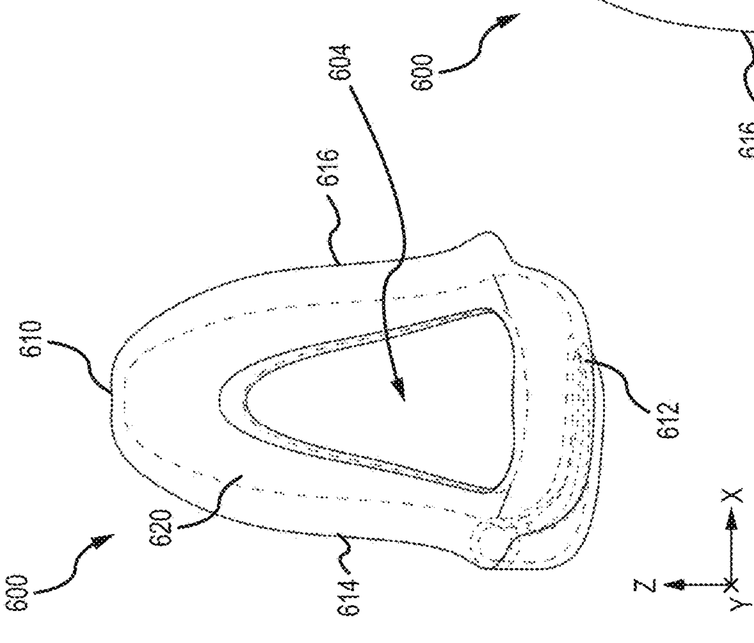
Figure 6I:
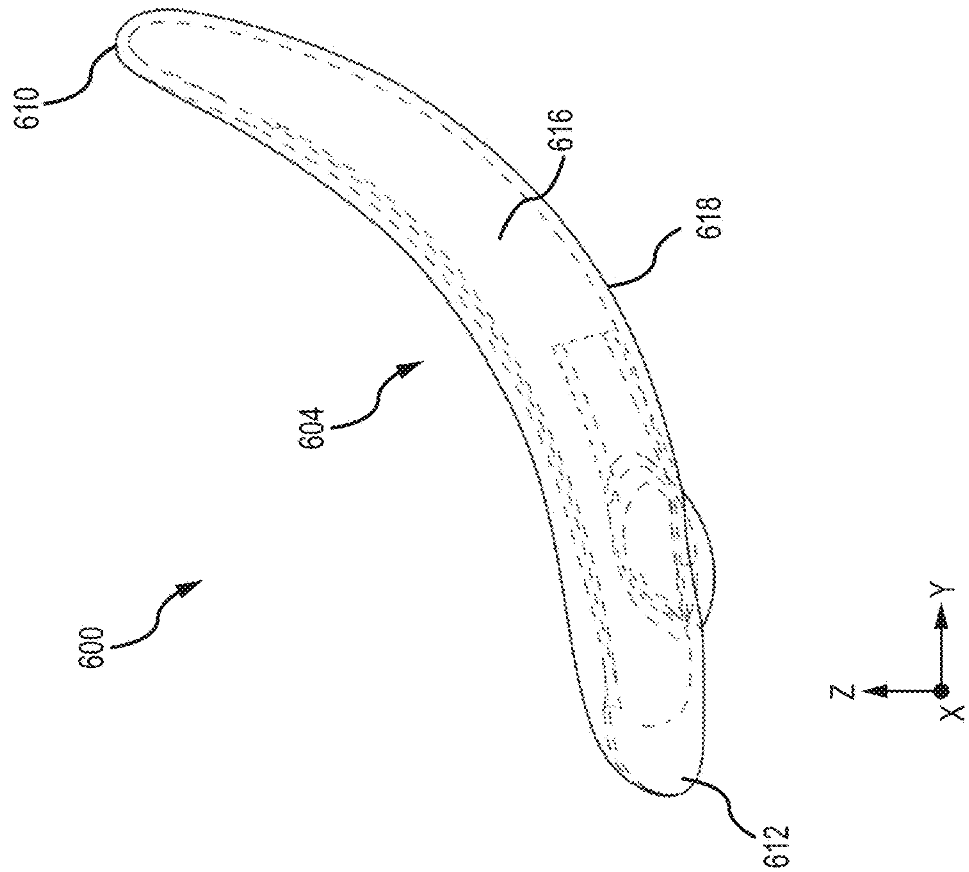
Figure 6H:
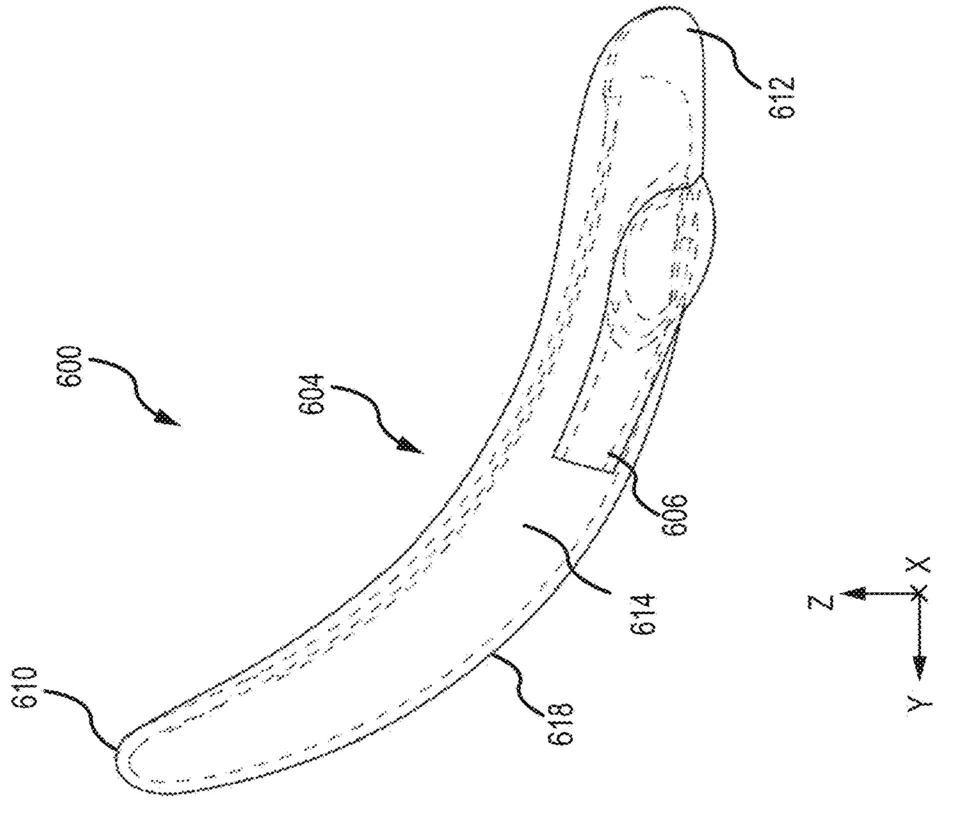
Figure 6K:
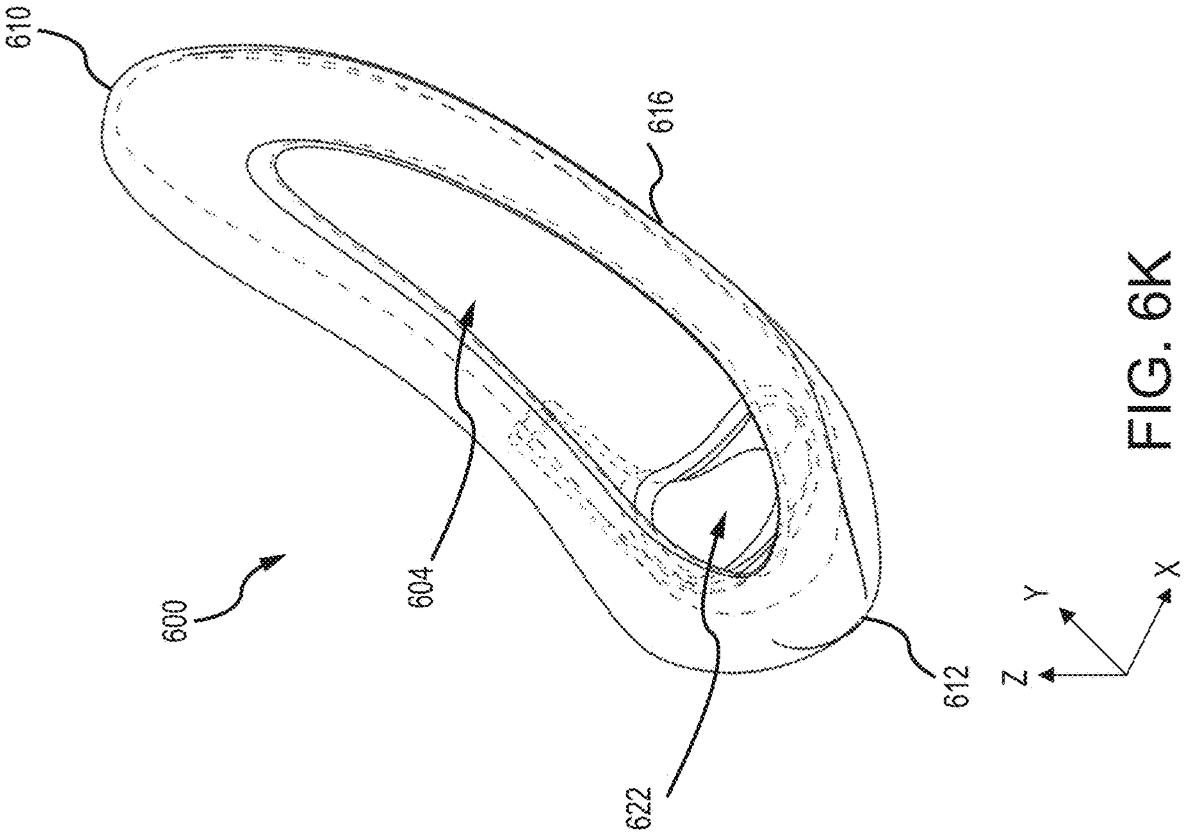
Figure 6J:
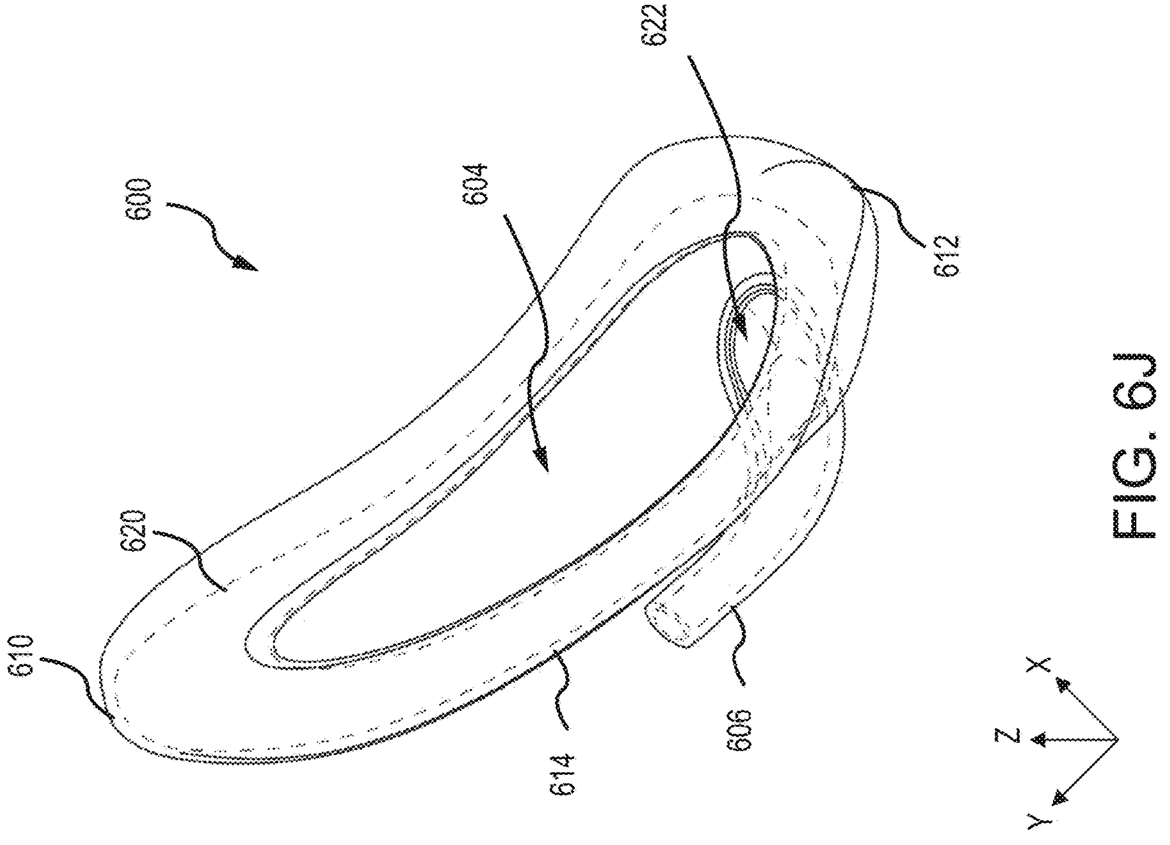
Figure 6M:
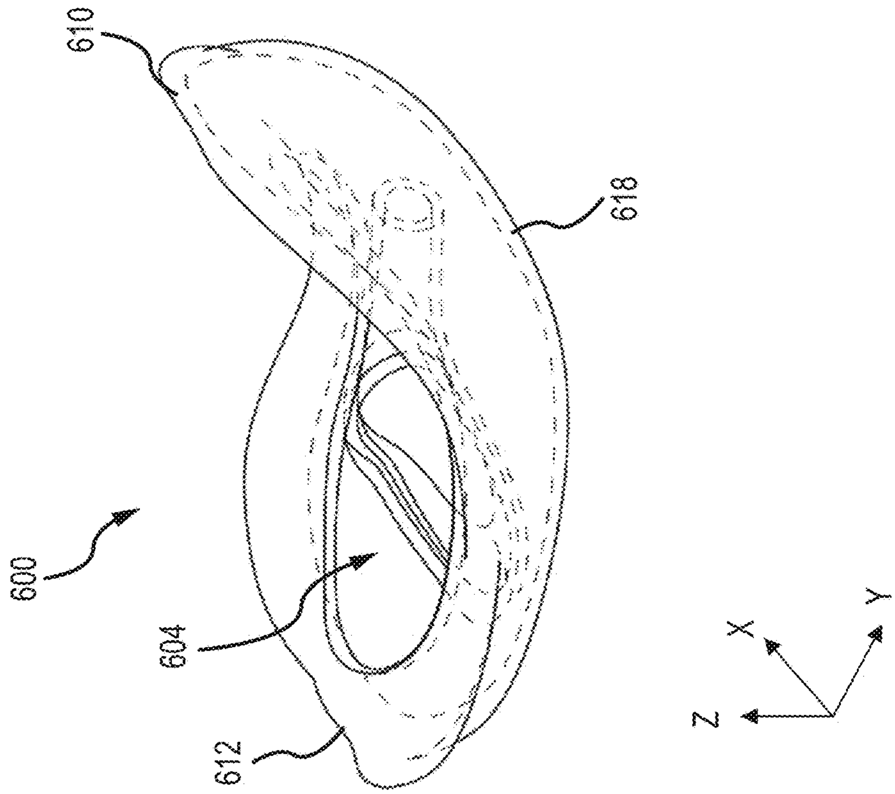
Figure 6L:
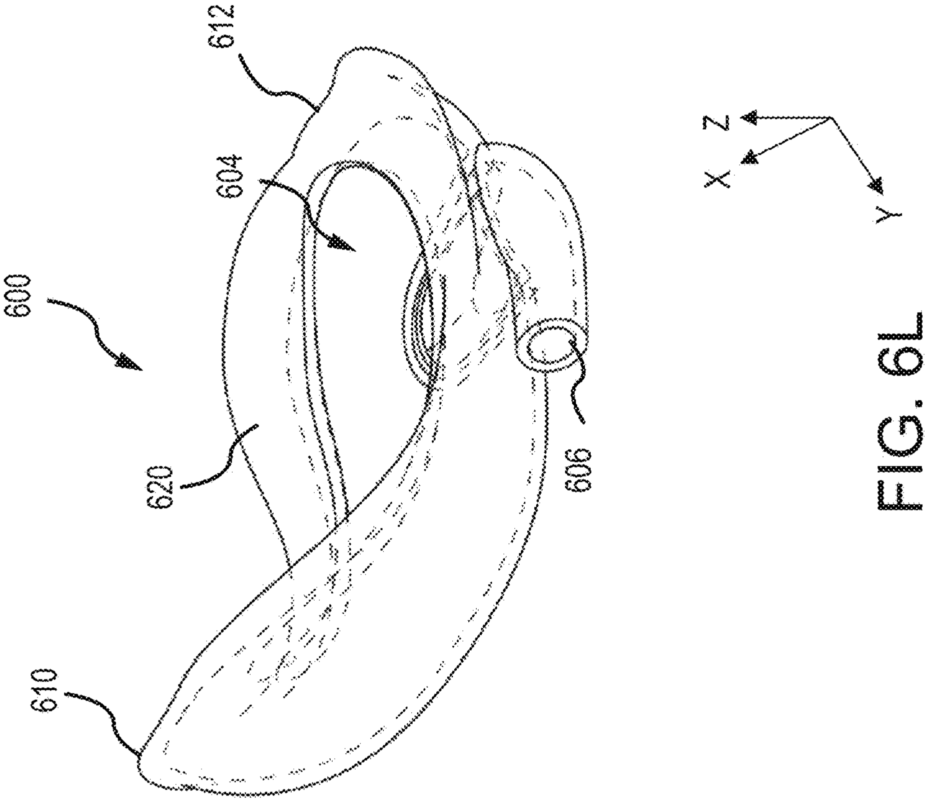

FIG. 6A illustrates a top view of human interface device 600, FIG. 6B illustrates a bottom view of human interface device 600, FIG. 6C illustrates of a perspective top view of human interface device 600, FIG. 6D illustrates a perspective bottom view of human interface device 600, FIG. 6E illustrates a front view of human interface device 600, FIG. 6F illustrates a back view of human interface device 600, FIG. 6G illustrates a perspective side view of human interface device 600, FIG. 6H illustrates a side view from the left side of human interface device 600, FIG. 6I illustrates a side view from the right side of human interface device 600, FIG. 6J illustrates an isometric north-east view (e.g., from a viewpoint rotated 225° and tilted 45°) of human interface device 600, FIG. 6K illustrates an isometric north-west view (e.g., from a viewpoint rotated 135° and tiled 45° from center), FIG. 6L illustrates an isometric south-east view (e.g., from a viewpoint rotated 315° and tilted 45° from center) of human interface device 600, and FIG. 6M illustrates an isometric south-west view (e.g., from a view point rotated 45° and tilted 45° from center).

Human interface device 600 includes similar components as human interface device 300 described above with respect to FIGS. 3A-3J, including a body 602, a fluid cavity 604, an outlet 606, a front 610, a back 612, a first side 614, a second side 616, a bottom 618, a top 620, and a funnel 622. The description of each of these may not be repeated below. Fluid cavity 604 is defined by body 602, and more specifically, by front 610, back 612, first side 614, second side 616, and bottom 618. Outlet 606 extends from fluid cavity 604 through body 602, and more specifically, through bottom 618 of body 602. Fluid cavity 604 is defined by a top 620 of body 602 which has an opening through which fluid (e.g., urine) enters fluid cavity 604. Funnel 622 is located in fluid cavity 604 and connects fluid cavity 604 to outlet 606. Outlet 606 is offset toward first side 614 (e.g., top the left of center) and near back 612 of body 602. Accordingly, funnel 622 is shaped to direct the fluid toward first side 614 and out through outlet 606. Outlet 606 extends toward front 610 of body 602, having an opening toward front 610. The fluid enters fluid cavity 604 through the opening in top 620, flows from fluid cavity 604 into funnel 622, and out of human interface device 600 through outlet 606 located along the left side of body 602 (e.g., near first side 614). In various embodiments, outlet 606 is fluidly coupled to a storage unit (e.g., storage device 206) by a hose, a tube, or other mechanism. In various embodiments, different motive forces (e.g., vacuum as described above with respect to FIG. 2) may transfer the liquid from human interface device 600, specifically through outlet 606, to the storage unit.

Human interface device 600 is configured to be worn by aircrew (e.g., pilot 102) while in a seated position. Accordingly, funnel 622 and outlet 606 are near back 612 of body 602 as body 602 will be tilted toward back 612 while the aircrew is seated. This allows the liquid in fluid cavity 604 to move toward funnel 622 to be evacuated, during normal flight operations. In various embodiments, the storage unit may be located on the left side of the aircrew (e.g., along first side 614) so that outlet 606 being located along first side 614 is more convenient for connecting outlet 606 to a hose and the storage unit. Additionally, outlet 606 being located along the left side (e.g., first side 614) allows the aircrew to wear normal undergarments as outlet 606 extends out of the normal undergarments for connection to the storage unit. Top 620 has a front portion 620*a*, a back portion 620*b*, a first side portion 620*c*, and a second side portion 620*d*, corresponding to front 610, back 612, first side 614, and second side 616, respectively. Front portion 620*a* has a larger surface area than back portion 620*b*. Front 610 of body 602 may be used by the aircrew to adjust the position of human interface device 600 while in use. First side 614 and second side 616, including first side portion 620*c* and second side portion 620*d* of top 620, are curved inward (e.g., along the x-axis) between front 610 and back 612. This curve allows body 602 to contour to the body of the aircrew and accommodate the legs of the aircrew while human interface device 600 is in use. Additionally, body 602 has a curve upward (e.g., in the positive z-direction) from back 612 to front 610, to accommodate the anatomy of the user and provide a better fit. In various embodiments, back portion 620*b* includes a ridge, or bump, that can be felt by the user to indicate that human interface device 600 is in the correct position (e.g., along the y-axis and/or along the x-axis) to be used.

Human interface device 600 may be formed as a single monolithic component such that all components of body 602 are formed together. In various embodiments, top 620 may be formed independent of the remainder of body 602 and coupled to body 602. Body 602 may be formed of a material that is flexible, and in various embodiments skin-safe, while maintaining its shape, such as plastic, rubber, vinyl, polyurethane, polylactic acid (PLA), acrylonitrile butadiene styrene (ABS), or silicone, among others. In various embodiments, body 602 may become more flexible in response to the heat from the body of the user while in use.

Figure 7B:
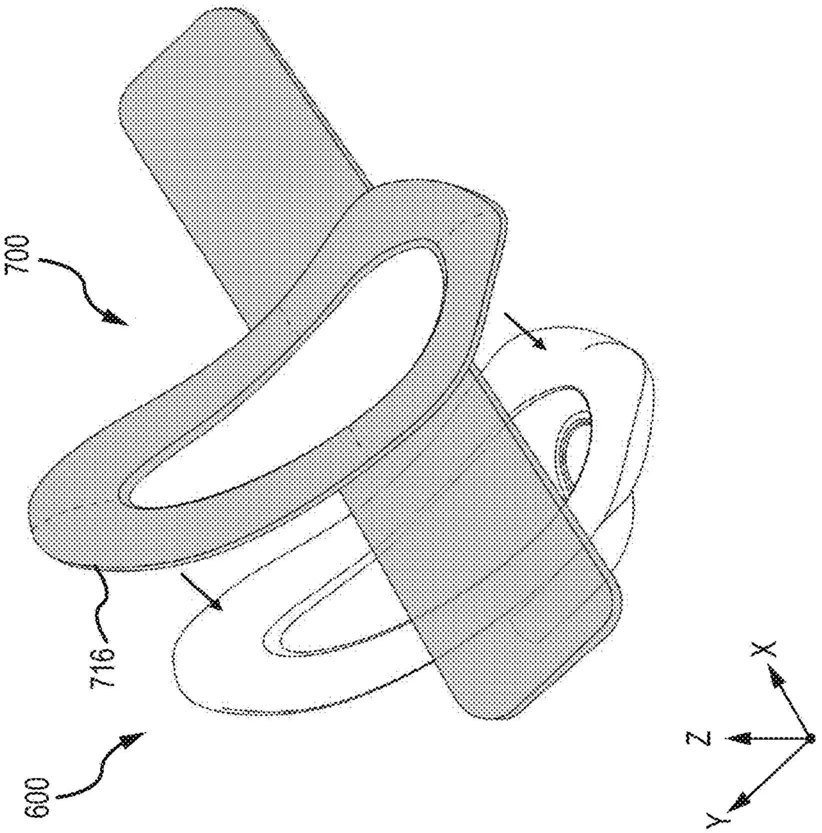
FIGS. 7A and 7B illustrate a pad for use with a human interface device in a urinary relief system, in accordance with various embodiments.
Figure 7A:
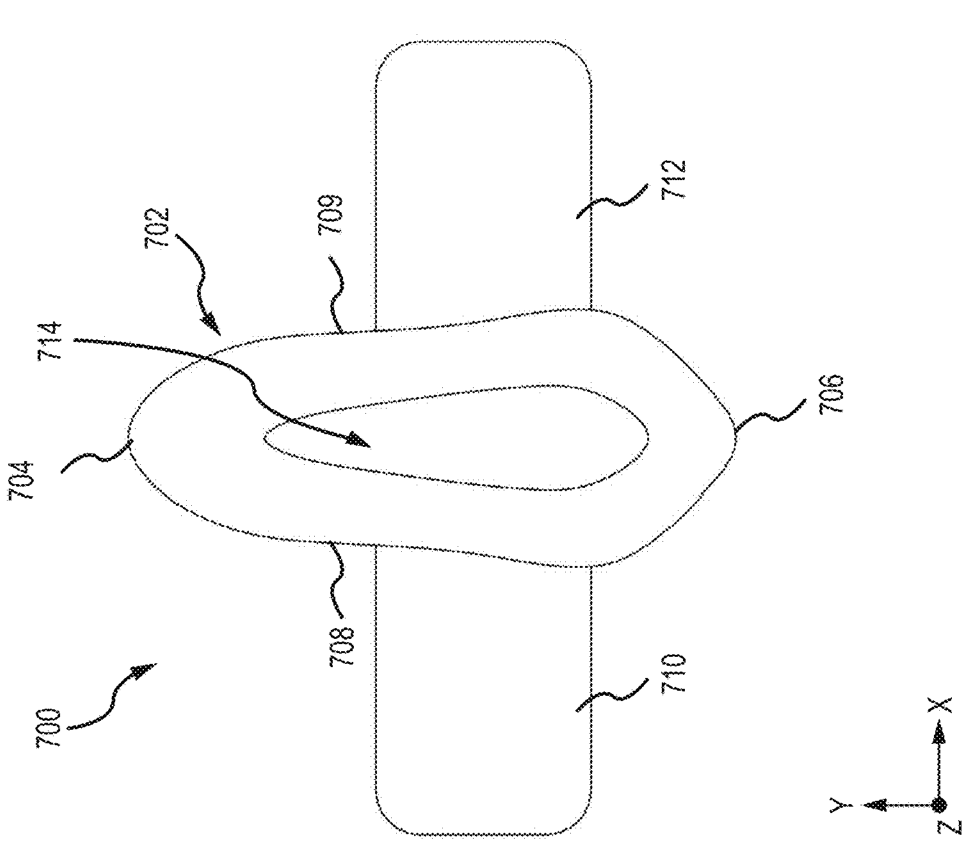

Referring now to FIGS. 7A and 7B, a pad 700 for use with human interface device 600 is illustrated, in accordance with various embodiments. FIG. 7A illustrates pad 700 and FIG. 7B illustrates pad 700 being joined to human interface device 600. Pad 700 includes similar features to those described above with respect to pad 400 in FIGS. 4A-4C, including a body 702, a first wing 710, and a second wing 712. Pad 700 may be made from similar materials as those described above with respect to pad 400.

Body 702 has an oval shape and is configured to match the shape of top 620 of human interface device 600. Accordingly, body 702 has a front 704, a back 706, a first side 708, and a second side 709 that correspond to front 610, back 612, first side 614, and second side 616, respectively. Body 702 of pad 700 defines an opening 714 that corresponds with the opening in top 620 of human interface device 600. Pad 700 further includes a bottom 716 that, when pad 700 is installed on human interface device 600, physically contacts top 620 of human interface device 600. In various embodiments, bottom 716 of pad 700 may include an adhesive material that secures pad 700 to human interface device 600. In various embodiments, wings 710, 712 may be used to secure pad 700 to human interface device 600.

When attached to human interface device 600, pad 700 provides additional comfort to the user during use as well as moisture wicking capabilities. That is, pad 700 may include absorbent materials similar to those described above with respect to pad 400. The absorbent materials may draw moisture away from the user to improve the comfort of human interface device 600 during use.

Figure 8B:
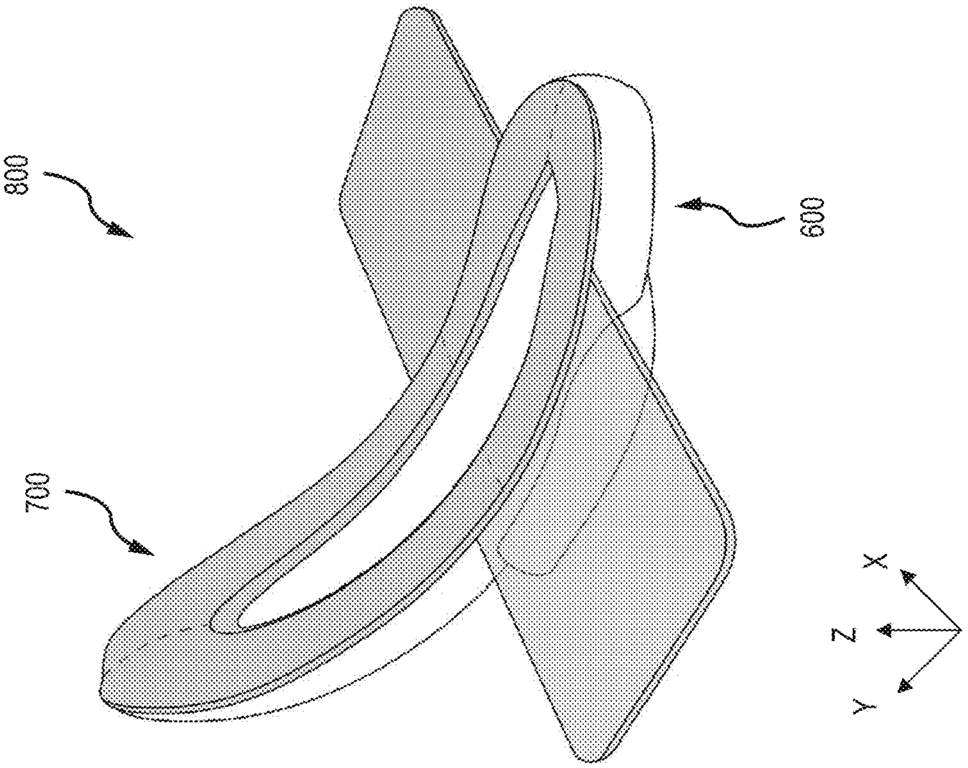
FIGS. 8A and 8B illustrate an assembled pad and human interface device for use with a urinary relief system, in accordance with various embodiments.
Figure 8A:
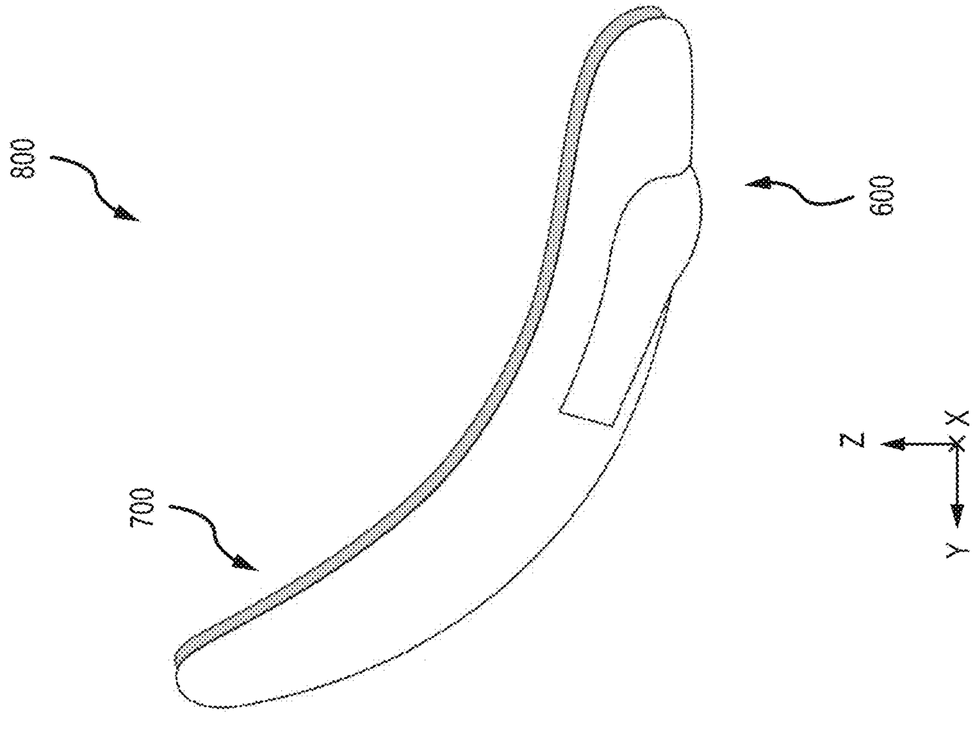

Referring now to FIGS. 8A and 8B, a human interface assembly 800 including human interface device 600 and pad 700 is illustrated, in accordance with various embodiments. FIG. 8A illustrates a side view of human interface assembly 800 and FIG. 8B illustrates a perspective view of human interface assembly 800. As described above, pad 700 is coupled to human interface device 600 (e.g., adhesive) to improve comfort (e.g., pad 700 using softer material than human interface device 600), reduce liquid splash back during use, secure human interface device 600 to the user, and to keep user dry during use, among other benefits. In various embodiments, first wing 710 and second wing 712 may include a first adhesive to secure first wing 710 to first side 614 and second wing 712 to second side 616. In various embodiments, first wing 710 and second wing 712 may include a second adhesive to secure first wing 710 and second wing 712 to the user (e.g., the garments and/or underwear of the user).

Figure 9B:
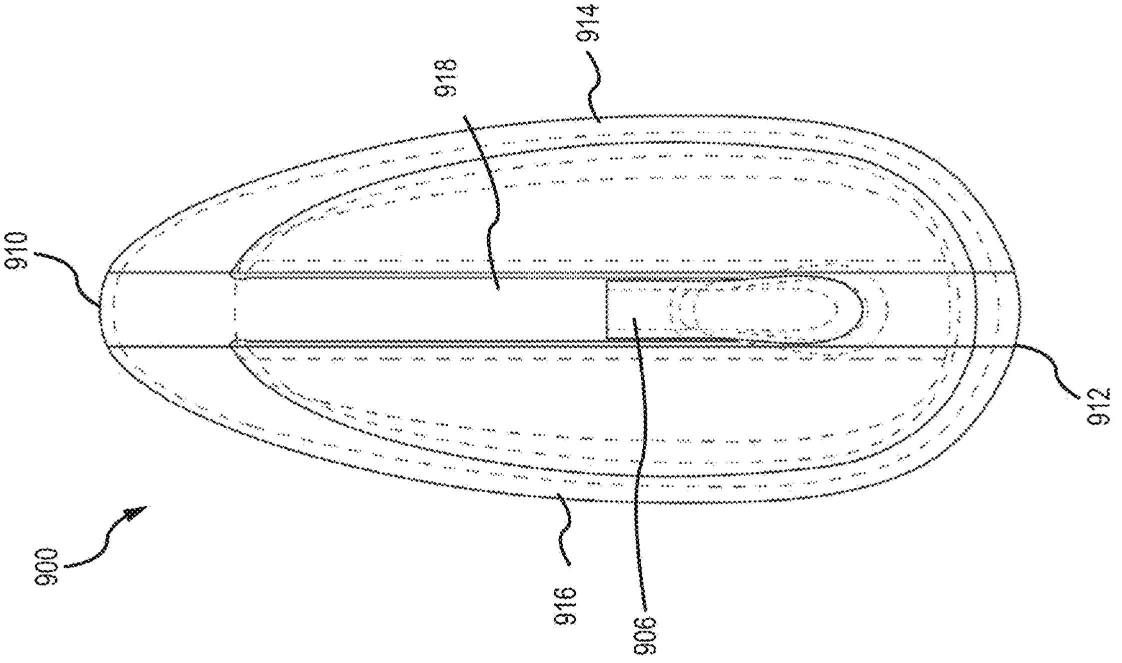
FIGS. 9A, 9B, 9C, 9D, 9E, 9F, 9G, 9H, and 9I illustrate a human interface device for use with a urinary relief system, in accordance with various embodiments.
Figure 9A:
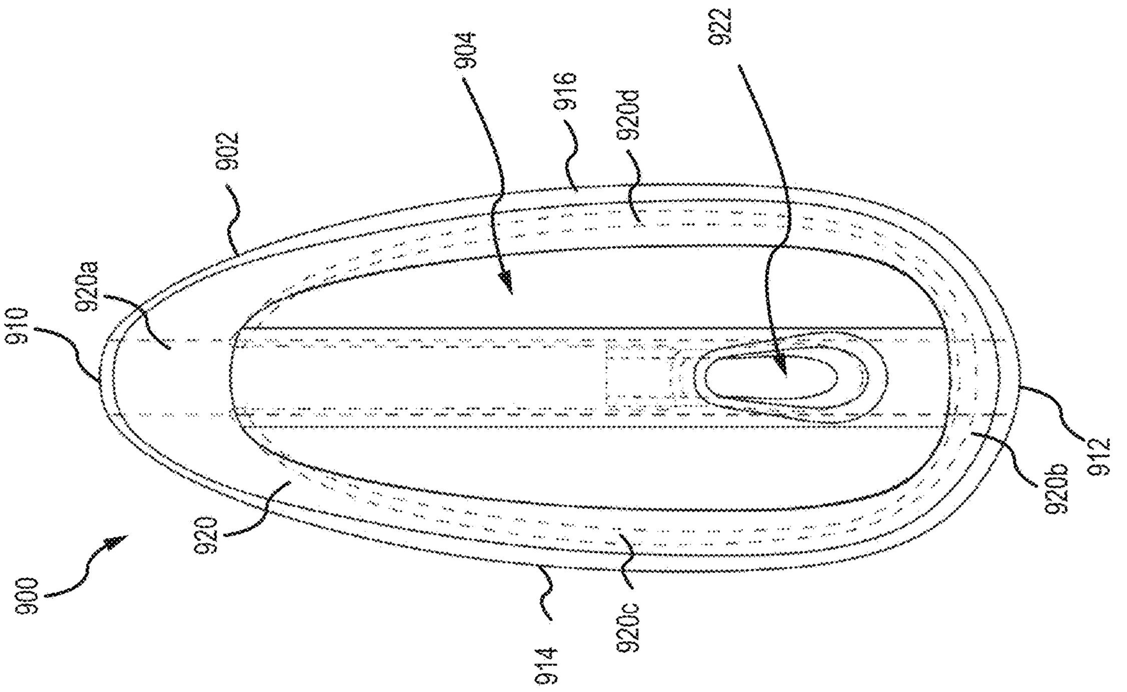
Figure 9D:
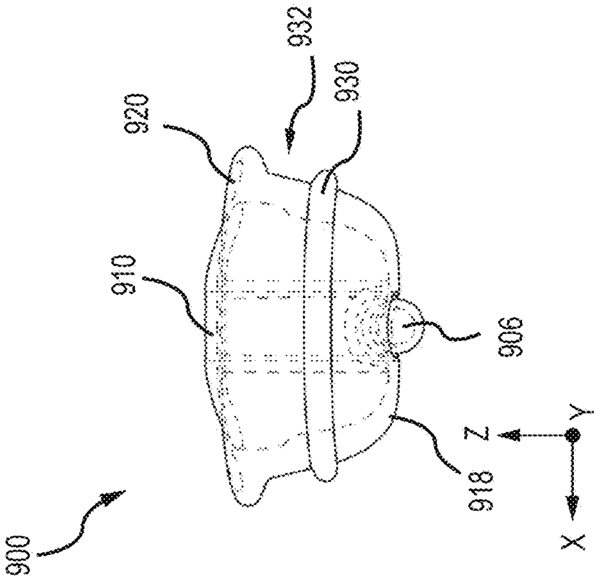
Figure 9E:
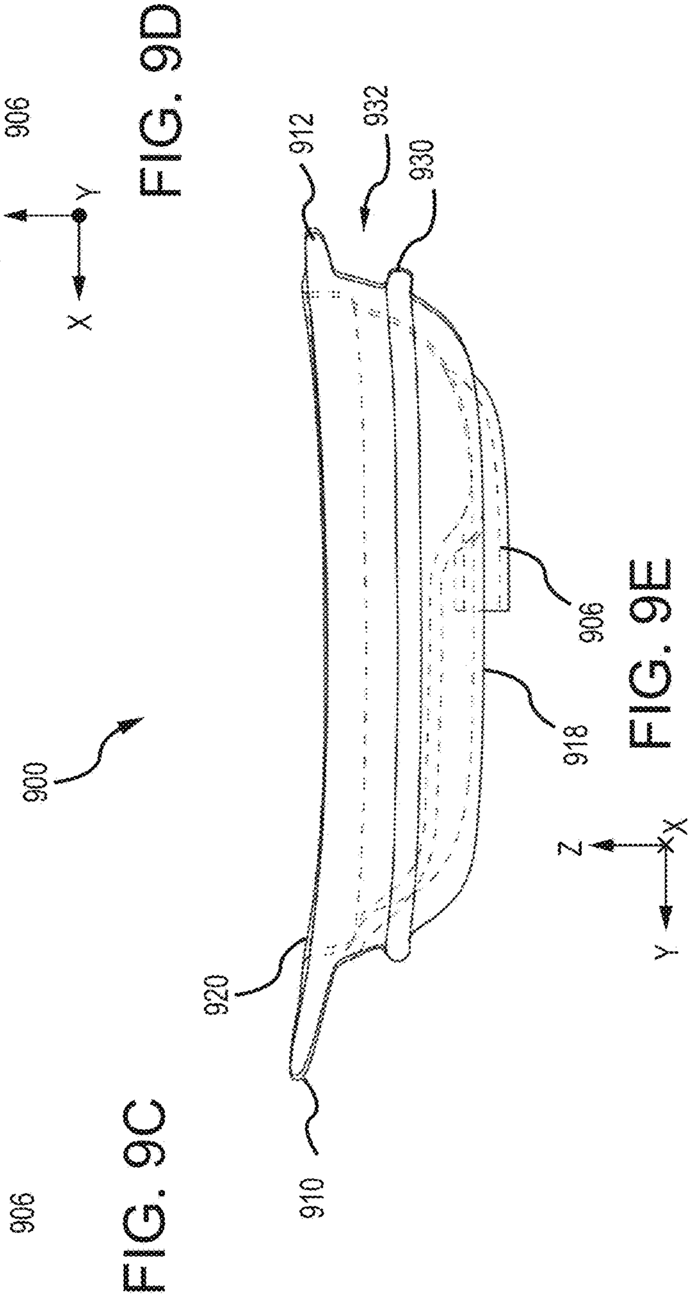
Figure 9C:
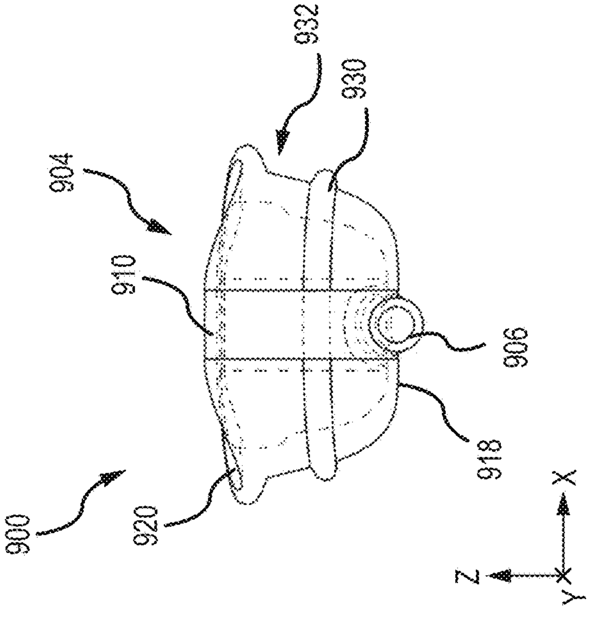
Figure 9G:
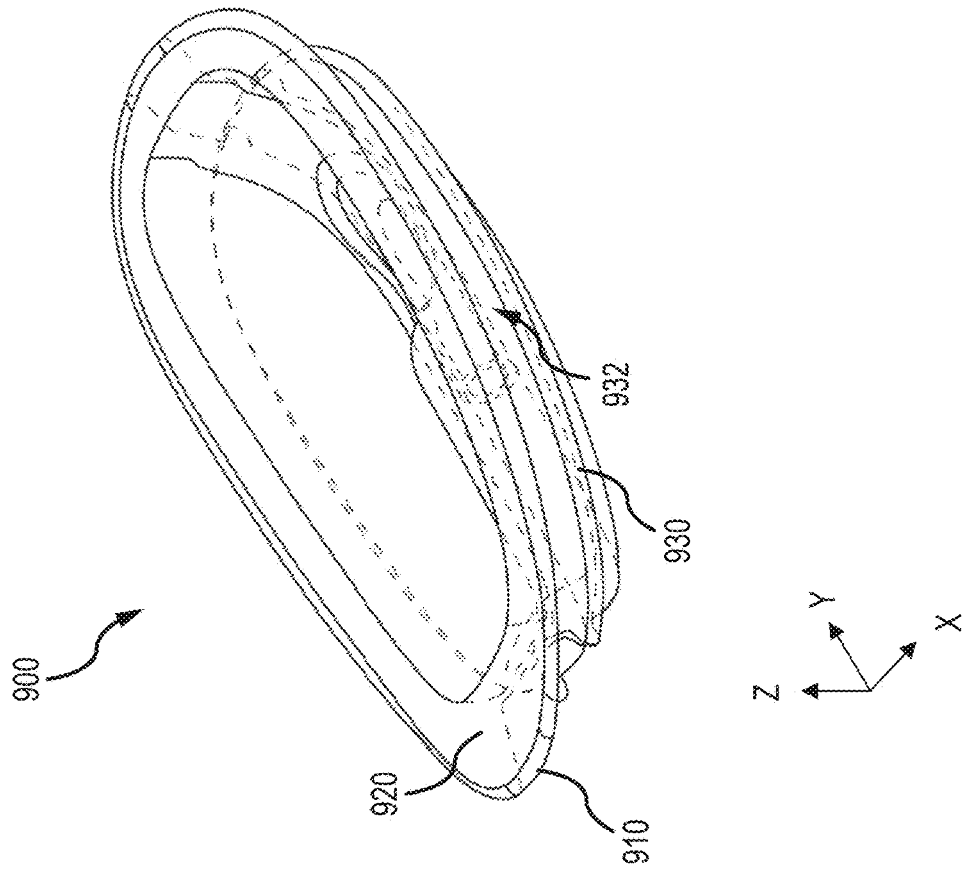
Figure 9F:
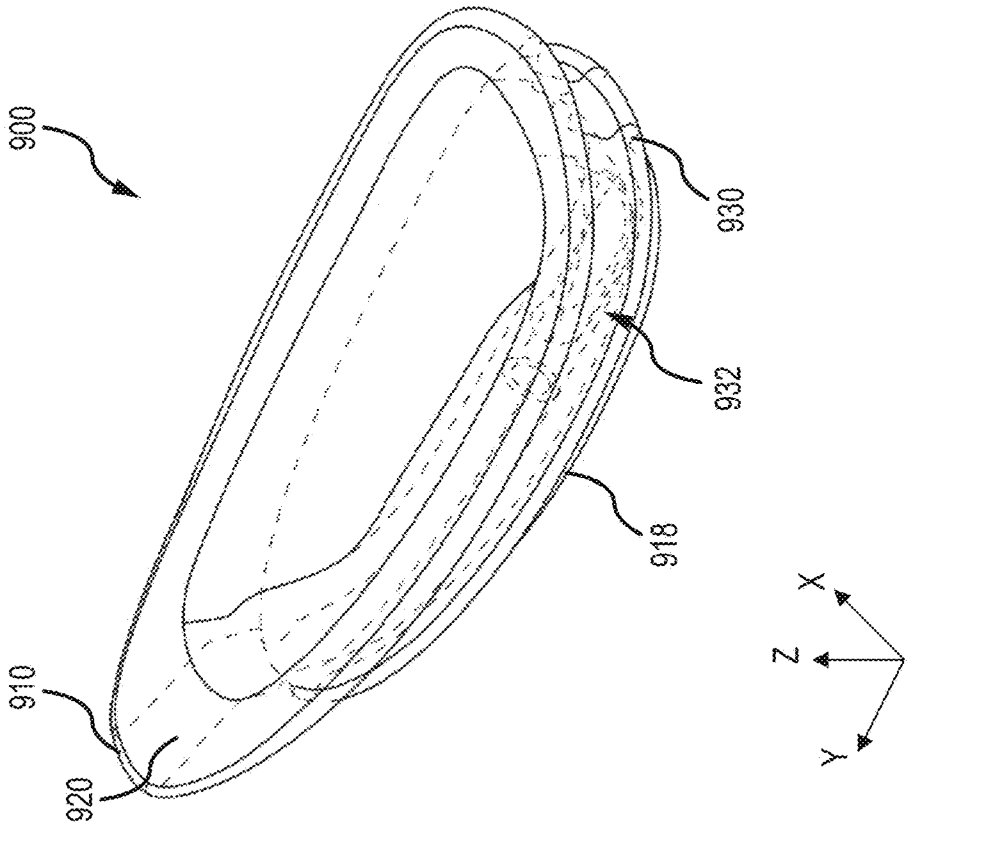
Figure 9H:
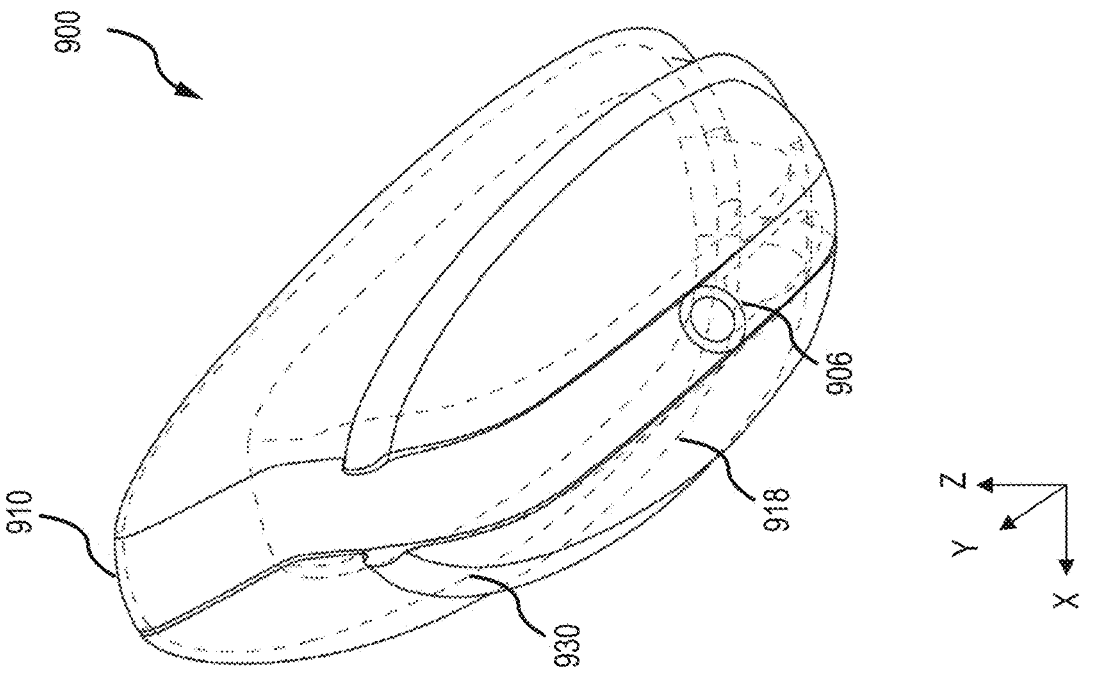
Figure 9I:
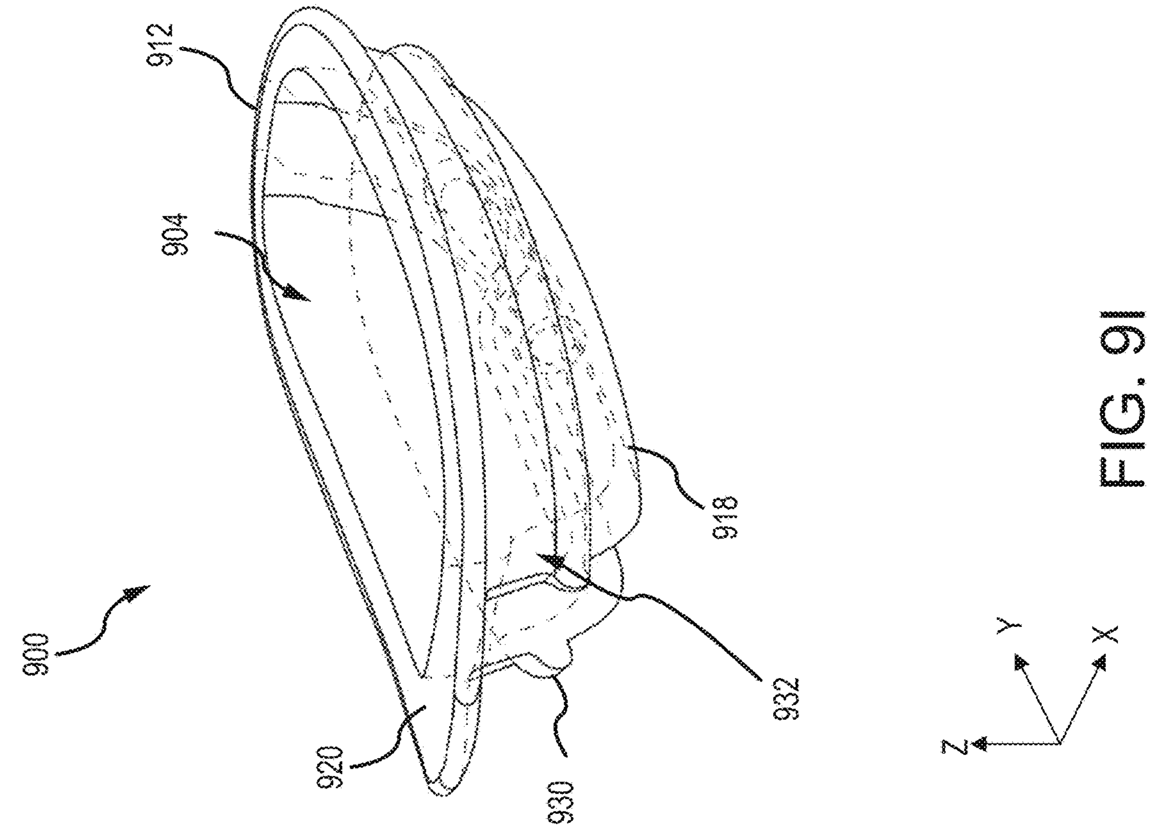

Referring now to FIGS. 9A-9I, a human interface device 900 is illustrated, in accordance with various embodiments. In various embodiments, human interface device 900 may be an example of human interface device 104 described above with respect to FIGS. 1A and 1B. In various embodiments, human interface device 900 may be an example of collection device 204 described above with respect to FIG. 2. FIG. 9A illustrates a top view of human interface device 900, FIG. 9B illustrates a bottom view of human interface device 900, FIG. 9C illustrates of a front view of human interface device 900, FIG. 9D illustrates a back view of human interface device 900, FIG. 9E illustrates a side view of human interface device 900, FIG. 9F illustrates an isometric north-east view (e.g., from a viewpoint rotated 225° and tilted 45° from center) of human interface device 900, FIG. 9G illustrates an isometric south-east view (e.g., from a viewpoint rotated 915° and tilted 45° from center) of human interface device 900, FIG. 9H illustrates a perspective front view of human interface device 900, and FIG. 9I illustrates a perspective bottom view of human interface device 900.

Human interface device 900 includes similar components as human interface device 300 described above with respect to FIGS. 3A-3J, including a body 902, a fluid cavity 904, an outlet 906, a front 910, a back 912, a first side 914, a second side 916, a bottom 918, a top 920, and a funnel 922. The description of each of these may not be repeated below. Fluid cavity 904 is defined by body 902, and more specifically, by front 910, back 912, first side 914, second side 916, and bottom 918. Outlet 906 extends from fluid cavity 904 through body 902, and more specifically, through bottom 918 of body 902. Outlet 906 extends toward front 910 of body 902, having an opening toward front 910. Fluid cavity 904 is defined by top 920 of body 902 which has an opening through which fluid (e.g., urine) enters fluid cavity 904. Funnel 922 is located in fluid cavity 904 and connects fluid cavity 904 to outlet 906. Outlet 906 is centered between first side 914 and second side 916 and near back 912 of body 902. Accordingly, funnel 922 is shaped to direct the fluid from fluid cavity 904 and out through outlet 906. The fluid enters fluid cavity 904 through the opening in top 920, flows from fluid cavity 904 into funnel 922, and out of human interface device 900 through outlet 906. In various embodiments, outlet 906 is fluidly coupled to a storage unit (e.g., storage device 206) by a hose, a tube, or other mechanism. In various embodiments, different motive forces (e.g., vacuum as described above with respect to FIG. 2) may transfer the liquid from human interface device 900, specifically through outlet 906, to the storage unit.

Human interface device 900 is configured to be worn by aircrew (e.g., pilot 102) while in a seated position. Accordingly, funnel 922 and outlet 906 are near back 912 of body 902 as body 902 will be tilted toward back 912 while the aircrew is seated. This allows the liquid in fluid cavity 904 to move toward funnel 922 to be evacuated, during normal flight operations. Top 920 has a front portion 920*a*, a back portion 920*b*, a first side portion 920*c*, and a second side portion 920*d*, corresponding to front 910, back 912, first side 914, and second side 916, respectively. Front portion 920*a* has a larger surface area than back portion 920*b*. Front 910 of body 902 may be used by the aircrew to adjust the position of human interface device 900 while in use.

In contrast to previously described embodiments, first side 914 and second side 916 are not curved inward (e.g., along the x-axis) between front 910 and back 912. Additionally, body 902 does not have an upward curve (e.g., in the positive z-direction) from back 912 to front 910 of body 902. Instead, body 902 as a gentle dip between back 912 and front 910, but back 912 and front 910 are at generally the same height (e.g., in the positive z-direction) as illustrated in FIG. 9E. This results in body 902 being boxier than previously described embodiments. This boxier design may be preferred by various aircrew depending on body type. Additionally, as described above, human interface device 900 may be formed from materials that are flexible and/or become flexible during use (e.g., from the body heat of the user). Body 902 may be formed from similar materials as those described above with respect to human interface device 300, 600.

Body 902 further includes a ring 930 that is formed around the outer circumference of body 902 between bottom 918 and top 920. In various embodiments, ring 930 may be formed about half-way between bottom 918 and top 920. In various embodiments, ring 930 may be formed more towards top 920 than bottom 918. The space between top 920 and ring 930 defines a channel 932 that extends around the outer circumference of body 902.

Figure 10B:
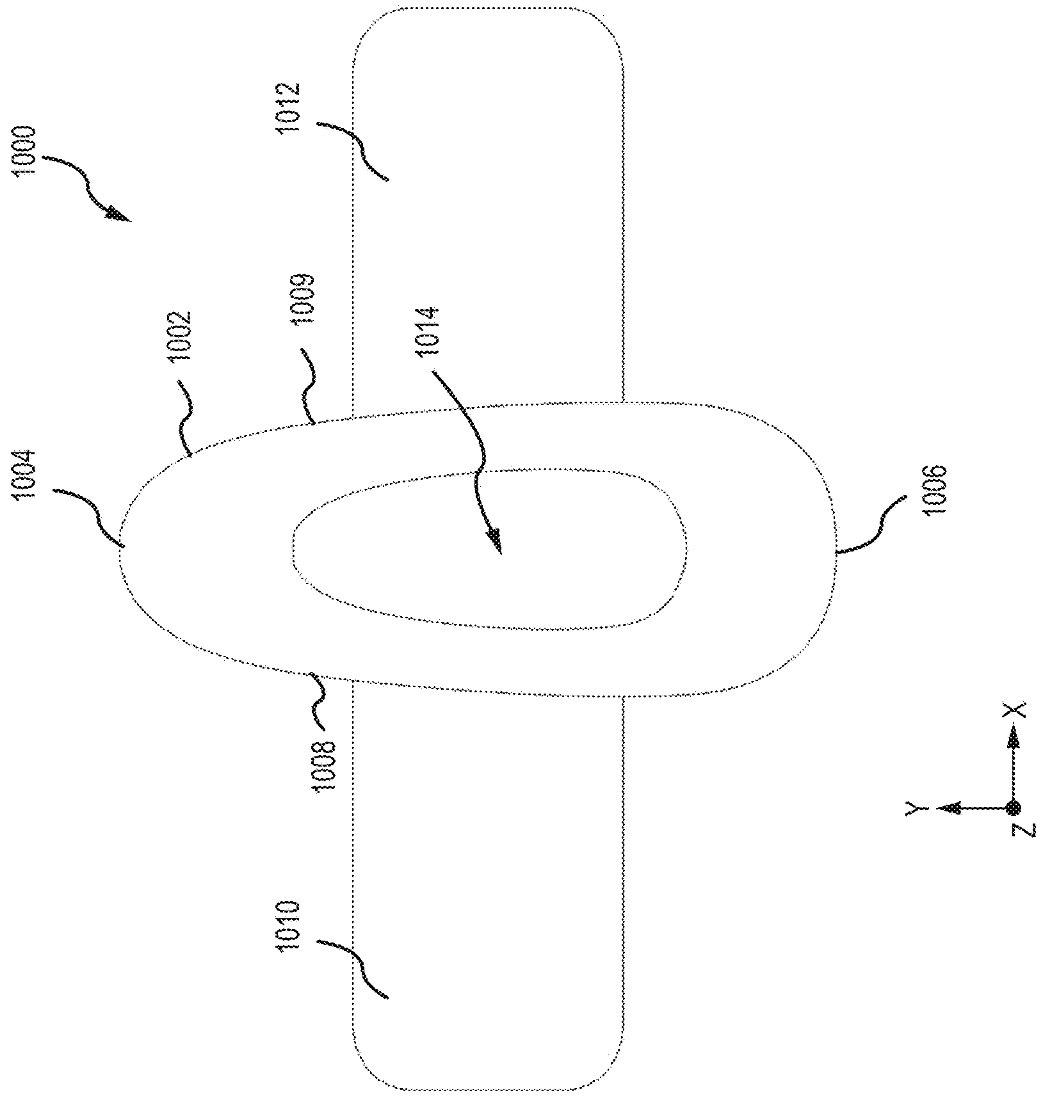
FIGS. 10A, 10B, and 10C illustrate a pad for use with a human interface device in a urinary relief system, in accordance with various embodiments.
Figure 10A:
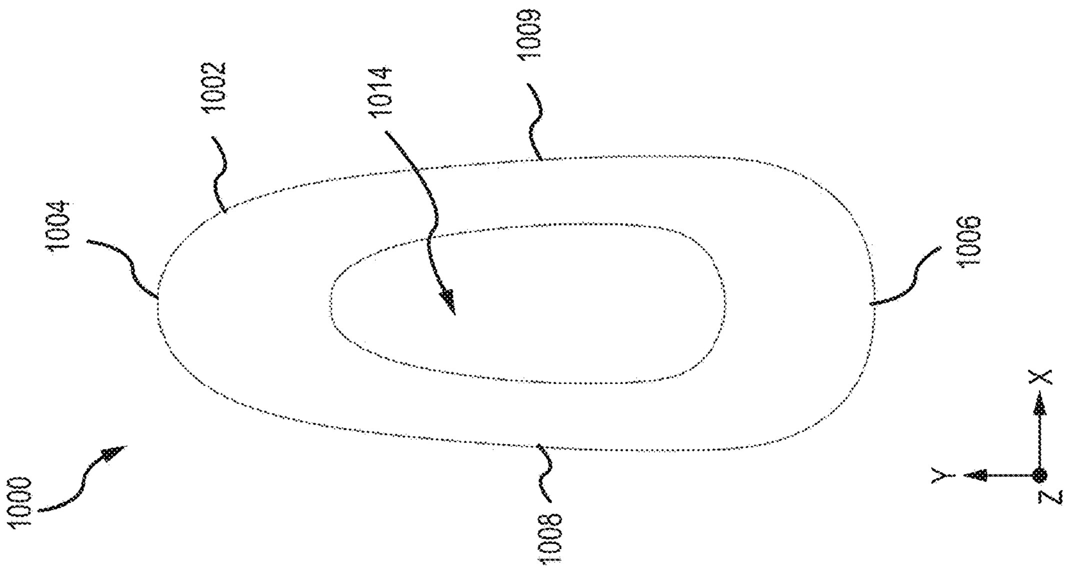
Figure 10C:
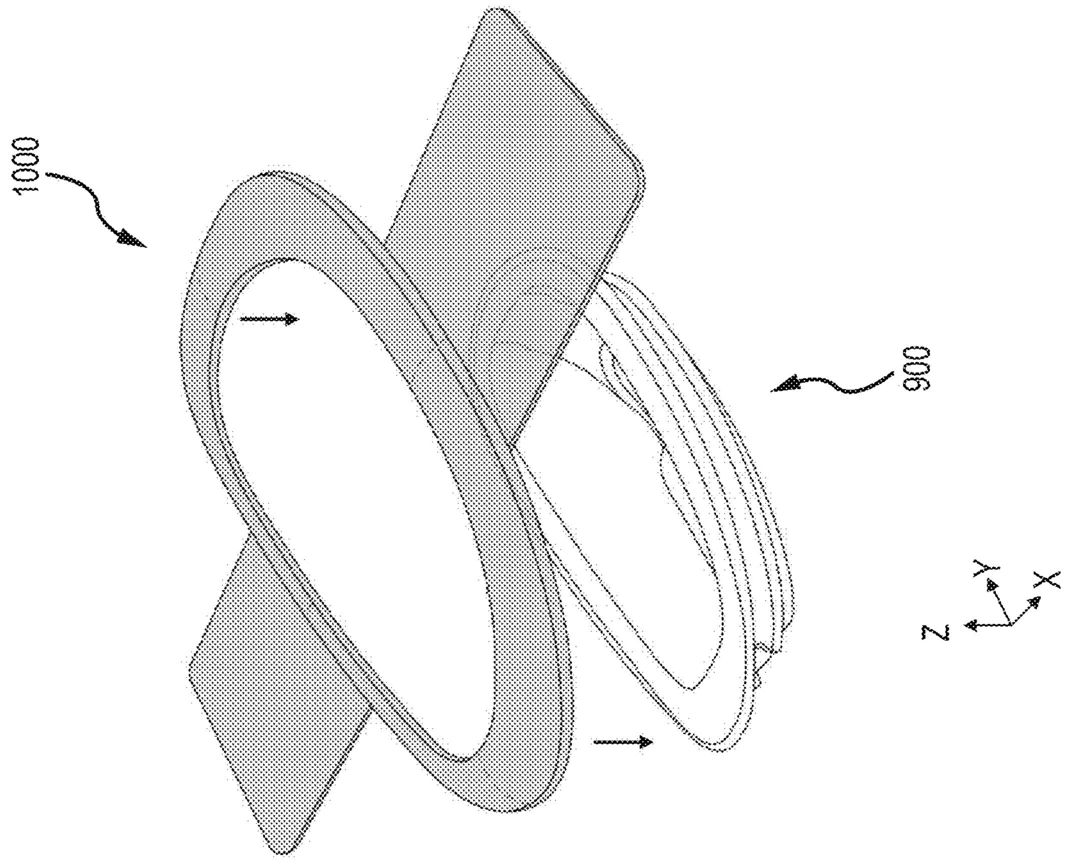

Referring now to FIGS. 10A-10C, a pad 1000 for use with human interface device 900 is illustrated, in accordance with various embodiments. FIG. 10A illustrates pad 1000 without wings, FIG. 10B illustrates pad 1000 with wings, and FIG. 10C illustrates pad 1000 being attached to human interface device 900.

Pad 1000 includes similar features to those described above with respect to pad 700 in FIGS. 7A and 7B, including a body 1002, a front 1004, a back 1006, a first side 1008, a second side 1009, and an opening 1014. In various embodiments, pad 1000 may include a first wing 1010, and a second wing 1012. Pad 1000 may be made from similar materials as those described above with respect to pad 400.

Body 1002 has an oval shape and is configured to match the shape of top 920 of human interface device 900. Accordingly, front 1004, back 1006, first side 1008, and second side 1009 that correspond to front 610, back 612, first side 614, and second side 616, respectively. Body 1002 of pad 1000 defines opening 1014 that corresponds with the opening in top 920 of human interface device 900. Opening 1014 may be larger than the opening of top 920 to allow pad 1000 to slide over top 920 and into channel 932. In various embodiments, pad 1000 may include an adhesive material around the interior of opening 1014 that secures pad 1000 to human interface device 900. In various embodiments, wings 1010, 1012 may be used to secure pad 1000 to the user.

Figure 11B:
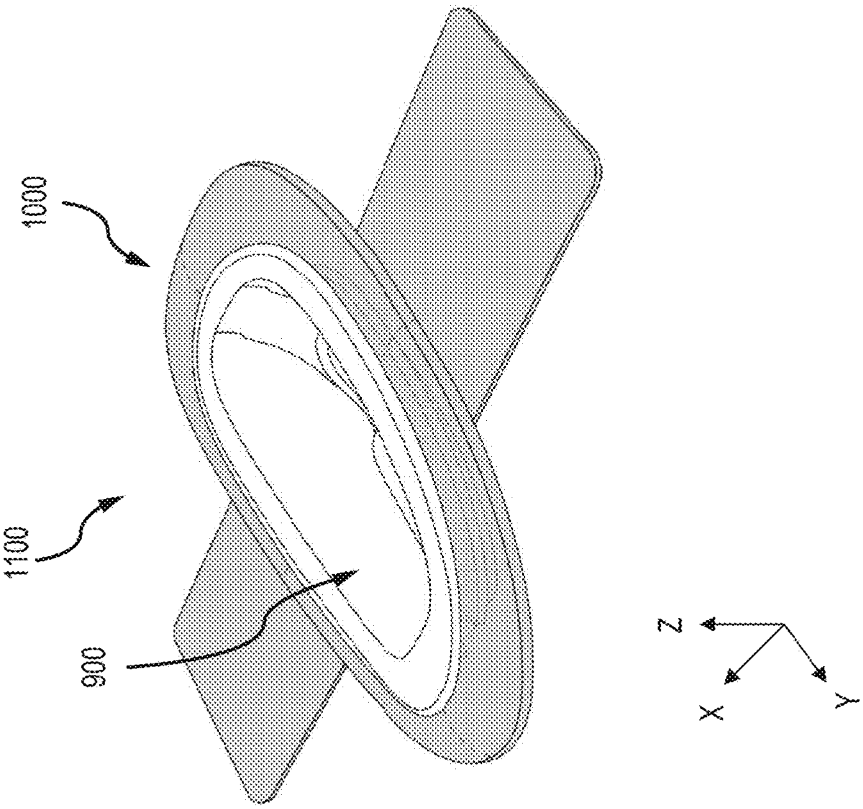
FIGS. 11A and 11B illustrate an assembled pad and human interface device for use with a urinary relief system, in accordance with various embodiments.
Figure 11A:
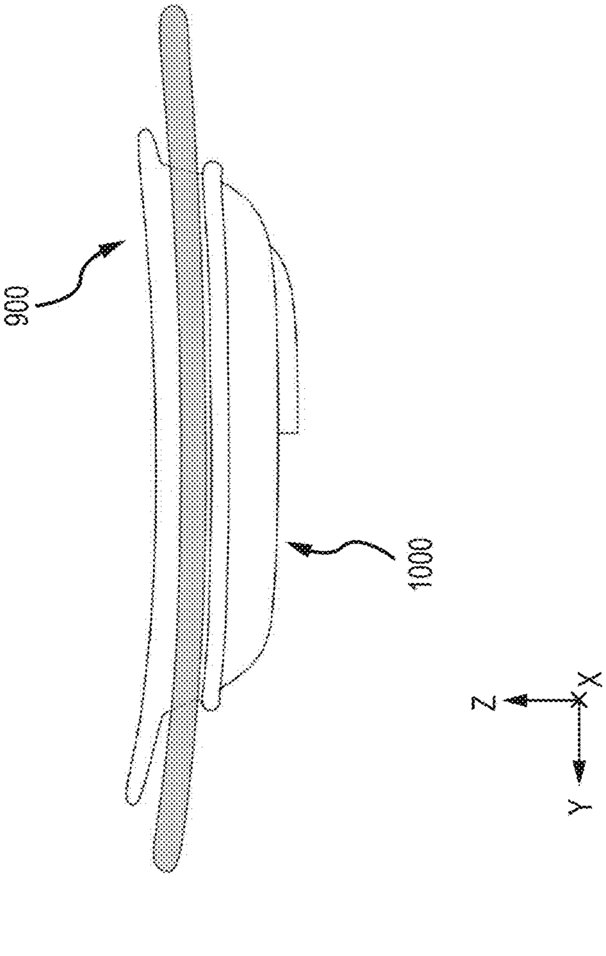

Referring now to FIGS. 11A and 11B, a human interface assembly 1100 including human interface device 900 and pad 1000 is illustrated, in accordance with various embodiments. FIG. 11A illustrates a side view of human interface assembly 1100 and FIG. 11B illustrates a perspective view of human interface assembly 1100. As described above, pad 1000 is coupled to human interface device 900 (e.g., securing in channel 932) to improve comfort, remove moisture, secure human interface device 900 to the user, and to keep user dry during use, among other benefits. In various embodiments, first wing 1010 and second wing 1012 may include an adhesive to secure first wing 1010 and second wing 1012 to the user (e.g., the garments and/or underwear of the user). In various embodiments, the relative proportions of body 1002 of pad 1000 may be changed to fit user preference and various anatomies, including being longer, wider, narrower, etc. It should be understood that various geometries and/or proportions of pad 1000 are contemplated so long as opening 1014 allows pad 1000 to assemble securely with human interface device 900, and more specifically, top 920.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process and may include values that are within 5% of a stated value. Additionally, the terms "substantially," "about" or "approximately" as used herein represent an amount close to the stated amount that still performs a desired function or achieves a desired result. For example, the term "substantially," "about" or "approximately" may refer to an amount that is within 5% of a stated amount or value.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above-described concepts can be used alone or in combination with any or all of the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A human interface for a urinary relief system, comprising:

a body including a top, a bottom, a front, a back, a first side, a second side, a first indent formed in the first side of the top of the body, and a second indent formed in the second side of the top of the body, the first indent configured to receive a first wing extending from a pad body, the second indent configured to receive a second wing extending from an opposing side of the pad body;

a fluid cavity defined by the bottom, the front, the back, the first side, and the second side, wherein the fluid cavity is an opening in the top of the body; and an outlet extending from the fluid cavity and through the bottom, the outlet located near the back and centered between the first side and the second side.

2. The human interface of claim 1, further comprising:

a funnel formed in the fluid cavity, the funnel located near the back, the outlet fluidly coupled to the fluid cavity through the funnel.

3. The human interface of claim 1, further comprising:

the pad having the pad body, the first wing extending from a first portion of the pad body and the second wing extending from a second portion of the pad body.

4. The human interface of claim 3, wherein the pad body includes a first end, a mid-point, and a second end, the first portion of the pad body extending from the first end to the mid-point, the second portion of the pad body extending from the mid-point to the second end, wherein the pad body is configured to fold about the mid-point.

5. The human interface of claim 4, wherein the pad is configured to be inserted into the fluid cavity and below the top of the body, the mid-point of the pad body being adjacent the front of the body, the first end and the second end of the pad body being adjacent the back.

6. The human interface of claim 3, wherein the pad body includes a pad front, a pad back, a first pad side, and a second pad side, the pad front, the pad back, the first pad side, and the second pad side defining a pad opening through the pad.

7. The human interface of claim 6, wherein the pad is configured to be coupled to the top of the body, the pad opening aligning with the opening in the top.

8. The human interface of claim 1, wherein the first side has a first curve extending toward the fluid cavity along the first side from the back to the front, and wherein the second side has a second curve extending toward the fluid cavity along the second side from the back to the front.

9. The human interface of claim 1, wherein the top is curved upward from the back to the front, the front being higher than the back.

10. A urinary relief system, comprising:

a control unit;

a storage device coupled to the control unit;

a human interface device coupled to the storage device, the human interface device including:

a tray including a top, a bottom, a front, a back, a first side, and a second side;

a fluid cavity defined by the bottom, the front, the back, the first side, and the second side, wherein the fluid cavity is an opening in the top of the tray;

an outlet extending from the fluid cavity and through the bottom and adjacent the back of the tray, the outlet extending toward the front of the tray; and a pad extending between a first side and a second side with a pad opening defined between the first side and the second side, wherein the pad comprises:

a first wing extending from the first side and configured to secure a position of the pad relative to the human interface device; and a second wing extending from the second side and configured to secure a position of the pad relative to the human interface device.

11. The urinary relief system of claim 10, wherein the outlet is centered between the first side and the second side.

12. The urinary relief system of claim 10, wherein the outlet is located adjacent the first side of the tray.

13. The urinary relief system of claim 10, wherein the pad has a linear body with a first end, a mid-point, and a second end, wherein the first wing extends from the first end to the mid-point and outward from the linear body, wherein the second wing extends from the mid-point to the second end and outward from the linear body, and wherein the pad is configured to be inserted into the fluid cavity, the first wing is configured to extend over the top on the first side, and the second wing is configured to extend over the top on the second side.

14. The urinary relief system of claim 10, wherein the pad has an oval body defining the pad opening, the pad configured to be coupled to the top of the tray such that the first wing extends from the first side of the pad and the second wing extends from the second side of the pad.

15. The urinary relief system of claim 10, wherein the pad is disposed around an outer surface of the tray and below the top of the tray.

16. The urinary relief system of claim 15, further comprising:

a ring formed around the outer surface of the tray and below the top of the tray; and a channel defined by the top of the tray and the ring, wherein the pad is located in the channel.

17. A human interface assembly, comprising:

a body having a front, a back, a bottom, a top, a first side, and a second side, the top having an opening formed therethrough, a first indent formed in the first side of the top of the body, and a second indent formed in the second side of the top of the body, the first indent configured to receive a first wing extending from a pad body, the second indent configured to receive a second wing extending from an opposing side of the pad body;

a fluid cavity formed in the body and defined by the front, the back, the bottom, the top, the first side, and the second side; and an outlet formed near the back of the body, the outlet extending from the fluid cavity and through the bottom of the body.

18. The human interface assembly of claim 17, further comprising:

the pad coupled to the body, wherein the pad is configured to be inserted into the fluid cavity and below the top of the body, wherein each of the first wing and the second wing are configured to extend over the top of the body.

19. The human interface assembly of claim 17, further comprising:

a funnel located near the back of the body, the funnel coupling the fluid cavity to the outlet, wherein the outlet extends out toward the first side of the body, the outlet including an outlet opening toward the front of the body.

* * * * *